United States Patent
Benavides et al.

(10) Patent No.: US 7,217,705 B2
(45) Date of Patent: *May 15, 2007

(54) COMBINATION OF A CB1 RECEPTOR ANTAGONIST AND OF A PRODUCT WHICH ACTIVATES DOPAMINERGIC NEUROTRANSMISSION IN THE BRAIN, THE PHARMACEUTICAL COMPOSITIONS COMPRISING THEM AND THEIR USE IN THE TREATMENT OF PARKINSON'S DISEASE

(75) Inventors: Jésus Benavides, Chatenay Malabry (FR); Daniel Boccio, Fayl-Billot (FR); Yvette Henin, Paris (FR); Odile Piot-Grosjean, Choisy le Roi (FR)

(73) Assignee: Aventis Pharma S.A., Paris (FR)

(*) Notice: Subject to any disclaimer, the term of this patent is extended or adjusted under 35 U.S.C. 154(b) by 219 days.

This patent is subject to a terminal disclaimer.

(21) Appl. No.: 10/786,810

(22) Filed: Feb. 25, 2004

(65) Prior Publication Data
US 2004/0209861 A1    Oct. 21, 2004

Related U.S. Application Data

(63) Continuation of application No. PCT/FR02/02946, filed on Aug. 28, 2002.

(30) Foreign Application Priority Data
Aug. 29, 2001  (FR) .................................. 01 11200

(51) Int. Cl.
*A01N 43/00* (2006.01)
*A01N 37/10* (2006.01)
*A01N 43/40* (2006.01)
*A01N 43/78* (2006.01)
*A61K 31/397* (2006.01)

(52) U.S. Cl. ............................ 514/210.01; 514/210.16; 514/252.12; 514/570; 514/323; 514/367

(58) Field of Classification Search ........... 514/210.21, 514/210.01
See application file for complete search history.

(56) References Cited

U.S. PATENT DOCUMENTS 5,562,917 A * 10/1996 Durif et al. ................. 424/447
6,355,631 B1 * 3/2002 Achard et al. ......... 514/210.21

OTHER PUBLICATIONS

Brotchie, J. M., The Cannabinoid Receptor Antagonist SR141716A Reduces L-DOPA- Induced Dyskinesia in the MPTP-Treated Primate Model of Parkinson's Disease, British Journal of Pharmacology (1998, vol. 123, pp. 66P).
Clara Sanudo-Pena et al., A Novel Neurotransmitter System Involved in the Control of Motor Behavior by the Basal Ganglia, Ann. New York Academy of Sciences, (1998, vol. 860, pp. 475-479).
Justin P. Meschler et al., D2, but not D1 Dopamine Receptor Agonists Potentiate Cannabinoid-Induced Sedation In Nonhuman Primates 1,2 Journal of Pharmacology And Experimental Therapeutics, (2000, vol. 292, Issue 3, pp. 952-959).
Vincenzo Di Marzo et al., Enhanced Levels of Endogenous Cannabinoids in the Globus Pallidus are Associated with a Reduction in Movement in an animal model of Parkinson's Disease, FASEB Journal (2000, vol. 14, Issue 10, pp. 1432-1438).

* cited by examiner

Primary Examiner—Sreeni Padmanabhan
Assistant Examiner—Yong S. Chong
(74) Attorney, Agent, or Firm—Balaram Gupta

(57) ABSTRACT

The present invention relates to the combination of one or more CB1 antagonist azetidine derivatives and of one or more products which activate dopaminergic neurotransmission in the brain, to the pharmaceutical compositions comprising them and to their use in the treatment of Parkinson's disease.

7 Claims, No Drawings

COMBINATION OF A CB1 RECEPTOR ANTAGONIST AND OF A PRODUCT WHICH ACTIVATES DOPAMINERGIC NEUROTRANSMISSION IN THE BRAIN, THE PHARMACEUTICAL COMPOSITIONS COMPRISING THEM AND THEIR USE IN THE TREATMENT OF PARKINSON'S DISEASE

This application is a continuation of International application No. PCT/FR02/02,946, filed Aug. 28, 2002; which claims the benefit of priority of French Patent Application No. 01/11,200, filed Aug. 29, 2001.

BACKGROUND OF THE INVENTION

1. Field of the Invention

The present invention relates to the combination of one or more CB1 receptor antagonists and of one or more products which activate dopaminergic neurotransmission in the brain, to the pharmaceutical compositions comprising them and to their use in the treatment of Parkinson's disease.

2. Description of the Art

CB1 receptor antagonists have been developed for the treatment of schizophrenia (D. Kendall, Curr. Opin. Cent. Peripher. Nerv. Syst. Invest. Drugs, 2(1), 112–122, 2000), for their effect on food intake (G. Colombo et al., Life Sciences, 63 (8), 113–117 (1998); J. Siamand et al., Behavioral Pharmacol., 9, 179–181 (1998)) and for the treatment of Parkinson's disease, epilepsy, migraine and stress (G. Gerdeman, D M. Lovinger, J. Neurophysiol., 85(1), 468–471, 2001; WO 0046209).

Parkinson's disease results from a chronic and progressive neurological disorder. It is based on a deficiency of dopamine and a relative excess of acetylcholine and is associated with destruction of the dopaminergic neurons which participate in the control of the motor activities (H. Lullmann et al., Atlas de poche de pharmacologie [Pocket atlas of pharmacology], 2nd Ed., Medecine-Sciences, Flammarion, ISBN2-257-12119-8). The treatment of Parkinson's disease is mainly pharmacological and involves various medicaments intended to increase the amount of dopamine present in the brain.

As dopamine does not pass through the hematoencephalic barrier, levodopa, a precursor of dopamine converted to dopamine by dopa decarboxylase, was developed in the 1960s. Levodopa remains today the first treatment of choice for Parkinson's disease and initially gives good results. However, after several years, fluctuations in response (on-off effect), a decrease in its effectiveness as the disease progresses (wearing-off effect) and in particular dyskinesias (involuntary abnormal movements) are observed in the majority of patients. A psychotic state may also be observed.

Other medicaments, such as dopaminergic agonists, are also recommended, alone or in combination with levodopa, and have as main aim that of reducing, at least, the undesirable effects of the latter. For some years, selective inhibitors of monoamine oxidase MAO-B, an enzyme which decomposes dopamine in the brain, and inhibitors of catechol-O-methyltransferase (COMT), an enzyme which prevents levodopa from crossing the hematoencephalic barrier, have been developed and prescribed in combination with levodopa. Significant side effects have also been observed with these therapies.

All of the references described herein are incorporated herein by reference in their entirety.

SUMMARY OF THE INVENTION

In order to overcome the abovementioned disadvantages, it has been found that the combination of one or more CB1 receptor antagonists and of one or more products which activate dopaminergic neurotransmission in the brain has a synergistic effect in the treatment of Parkinson's disease. This is because this combination would make it possible to potentiate the symptomatic effects of a dopaminergic monotherapy (levodopa, dopaminergic agonists and enzyme inhibitors) and would make it possible to reduce the side effects, in particular dyskinesias.

DETAILED DESCRIPTION OF THE INVENTION

In addition to levodopa, a precursor of dopamine, mention may be made, among dopaminergic agonists, of the following products: bromocriptine (Novartis), cabergoline (Pharmacia Corp.), adrogolide (Abbott Laboratories), BAM-1110 (Maruko Seiyaku Co. Ltd), Duodopa® (Neopharma), L-dopa, dopadose (Neopharma), CHF1512 (Chiesi), Neuro-Cell-PD (Diacrin Inc.), PNU-95666 (Pharmacia & Upjohn), ropinirole (GlaxoSmithKline Beecham), pramipexole (Boehringer Ingelheim), rotigotine (Discovery Therapeutics, Lohmann Therapy System), spheramine (Titan Pharmaceuticals), TV1203 (Teva Pharmaceutical) or uridine (Polifarma).

Mention may be made, among $MAO_B$ inhibitors, of: rasagiline (Teva Pharmaceutical Ind.), selegiline (RPScherer Corp./Elan) or SL340026 (Sanofi-Synthelabo).

Mention may be made, among COMT inhibitors, of: tolcapone (Roche) and entacapone (Orion Pharma).

A subject-matter of the invention is therefore the combination of one or more products which activate dopaminergic neurotransmission in the brain and of one or more CB1 antagonist azetidine derivatives of formula (I).

Use may in particular be made, among CB1 antagonists, of the azetidine derivatives disclosed in patent applications FR 0002775, FR 0002777 and FR 0002776 of formula (I):

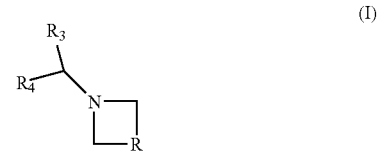

in which either A:

R represents a $CR_1R_2$, $C=C(R_5)SO_2R_6$ or $C=C(R_7)SO_2alk$ radical, either $R_1$ represents a hydrogen atom and $R_2$ represents a —$C(R_8)$ $(R_9)$ $(R_{10})$, —$C(R_8)$ $(R_{11})$ $(R_{12})$, —CO—$NR_{13}R_{14}$, —$CH_2$—CO—$NR_{13}R_{14}$, —$CH_2$—CO—$R_6$, —CO—$R_6$, —CO-cycloalkyl, —SO—$R_6$, —$SO_2$—$R_6$, —C(OH) $(R_{12})$ $(R_6)$, —C(OH) $(R_6)$ (alkyl), —C(=NOalk)$R_6$, —C(=NO—$CH_2$—CH=$CH_2$)$R_6$, —$CH_2$—CH($R_6$) $NR_{31}R_{32}$, —$CH_2$—C(=NOalk)$R_6$, —CH($R_6$)$NR_{31}R_{32}$, —CH($R_6$)$NHSO_2$alk, —CH($R_6$)NHCONHalk or —CH($R_6$) NHCOalk radical, or $R_1$ represents an alkyl, NH—$R_{15}$, cyano, —S-alk-$NR_{16}R_{17}$, —$CH_2$—$NR_{18}R_{19}$ or —$NR_{20}R_{21}$ radical and $R_2$ represents a —$C(R_8)$ $(R_{11})$ $(R_{12})$ radical, $R_3$ and $R_4$, which are identical or different, represent either an alkyl or cycloalkyl radical, or an aromatic radical chosen from phenyl, naphthyl or indenyl, these aromatic radicals being unsubstituted or substituted by one or more halogen, alkyl, alkoxy, formyl, hydroxyl, trifluoromethyl, trifluoromethoxy, —CO-alk, cyano, —COOH, —COOalk, —CONR$_{22}$R$_{23}$, —CO—NH—NR$_{24}$R$_{25}$, alkylsulfanyl, alkylsulfinyl, alkylsulfonyl, alkylsulfanylalkyl, alkylsulfinylalkyl, alkylsulfonylalkyl, hydroxyalkyl or -alk-NR$_{24}$R$_{25}$; or a heteroaromatic radical chosen from the benzofuryl, benzothiazolyl, benzothienyl, benzoxazolyl, chromanyl, 2,3-dihydroxybenzofuryl, 2,3-dihydrobenzothienyl, furyl, imidazolyl, isochromanyl, isoquinolyl, pyrrolyl, pyridyl, pyrimidinyl, quinolyl, 1,2,3,4-tetrahydroisoquinolyl, thiazolyl and thienyl rings, it being possible for these heteroaromatic radicals to be unsubstituted or substituted by one or more halogen, alkyl, alkoxy, hydroxyl, trifluoromethyl, trifluoromethoxy, cyano, —COOH, —COOalk, —CO—NH—NR$_{24}$R$_{25}$, —CONR$_{22}$R$_{23}$, -alk-NR$_{24}$R$_{25}$, alkylsulfanyl, alkylsulfinyl, alkylsulfonyl, alkylsulfanylalkyl, alkylsulfinylalkyl, alkylsulfonylalkyl or hydroxyalkyl, $R_5$ represents a hydrogen atom or an alkyl radical, $R_6$ represents an Ar$_1$ or Het$_1$ radical, $R_7$ represents a cycloalkyl, heterocycloalkyl or heterocyclenyl radical optionally substituted by a —CSO-phenyl radical, $R_8$ represents a hydrogen atom or an alkyl radical, $R_9$ represents a —CO—NR$_{26}$R$_{27}$, —COOH, —COOalk, —CH$_2$OH, —NH—CO—NH-alk, —CH$_2$—NHR$_{28}$ or —NHCOOalk radical, $R_{10}$ represents an Ar$_1$ or Het$_1$ radical, $R_{11}$ represents an —SO$_2$-alk, —SO$_2$—Ar$_1$ or —SO$_2$-Het$_1$ radical, $R_{12}$ represents a hydrogen atom or an Ar$_1$ or Het$_1$ radical, $R_{13}$ represents a hydrogen atom or an alkyl radical, $R_{14}$ represents an Ar$_1$, Het$_1$, -alk-Ar$_1$ or -alk-Het$_1$ radical, $R_{15}$ represents an alkyl, cycloalkyl or -alk-NR$_{29}$R$_{30}$ radical, $R_{16}$ and $R_{17}$, which are identical or different, represent a hydrogen atom or an alkyl radical or else $R_{16}$ and $R_{17}$ form, together with the nitrogen atom to which they are attached, a saturated or unsaturated and mono- or bicyclic heterocycle having 3 to 10 ring members and optionally comprising one or more other heteroatoms chosen from oxygen, sulfur and nitrogen and optionally substituted by one or more alkyl radicals, $R_{18}$ represents a hydrogen atom or an alkyl radical, $R_{19}$ represents a hydrogen atom or an alkyl, cycloalkyl, cycloalkylalkyl, cycloalkylcarbonyl, —SO$_2$alk, —CO—NHalk or —COOalk radical, or else, $R_{18}$ and $R_{19}$ form, with the nitrogen atom to which they are attached, a saturated or unsaturated and mono- or bicyclic heterocycle having 3 to 10 ring members and optionally comprising one or more heteroatoms chosen from oxygen, sulfur and nitrogen and optionally substituted by one or more alkyl radicals, —NR$_{20}$R$_{21}$ represents a saturated or unsaturated monocyclic heterocycle having 3 to 8 ring members and optionally comprising another heteroatom chosen from oxygen, nitrogen and sulfur, $R_{22}$ and $R_{23}$, which are identical or different, represent a hydrogen atom or an alkyl radical or else $R_{22}$ and $R_{23}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one more alkyl radicals, $R_{24}$ and $R_{25}$, which are identical or different, represent a hydrogen atom or an alkyl, —COOalk, cycloalkyl, alkylcycloalkyl, -alk-O-alk or hydroxyalkyl radical or else $R_{24}$ and $R_{25}$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$ radicals, $R_{26}$ and $R_{27}$, which are identical or different, represent a hydrogen atom or an alkyl, hydroxyalkyl, cycloalkyl, cycloalkylalkyl, -alk-COOalk, -alk-Ar$_1$, alk-Het$_1$, Het$_1$ or -alk-N(alk)$_2$ radical, $R_{26}$ and $R_{27}$ can also form, with the nitrogen atom to which they are attached, a saturated or unsaturated and mono- or bicyclic heterocycle having 3 to 10 ring members and optionally comprising one or more heteroatoms chosen from oxygen, sulfur and nitrogen and optionally substituted by one or more alkyl, alkoxy or halogen radicals, $R_{28}$ represents a —CH$_2$-alk, benzyl, —SO$_2$alk, —CONHalk, —COalk, cycloalkylalkylcarbonyl, cycloalkylcarbonyl or —CO—(CH$_2$)$_n$OH radical, n is equal to 1, 2, or 3, $R_{29}$ and $R_{30}$, which are identical or different, represent a hydrogen atom or an alkyl radical or else $R_{29}$ and $R_{30}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl radicals, $R_{31}$ and $R_{32}$, which are identical or different, represent a hydrogen atom or an alkyl, Ar$_1$ or -alk-Ar$_1$ radical or else $R_{31}$ and $R_{32}$ form, together with the nitrogen atom to which they are attached, a heterocycle chosen from aziridinyl, azetidinyl, pyrrolidinyl and piperidinyl, Ar$_1$ represents a phenyl or naphthyl radical optionally substituted by one or more substituents chosen from halogen, alkyl, alkoxy, —CO-alk, cyano, —COOH, —COOalk, —CONR$_{22}$R$_{23}$, —CO—NH—NR$_{24}$R$_{25}$, alkylsulfanyl, alkylsulfinyl, alkylsulfonyl, alkylsulfanylalkyl, alkylsulfinylalkyl, alkylsulfonylalkyl, hydroxyalkyl, -alk-NR$_{24}$R$_{25}$, —NR$_{24}$R$_{25}$, alkylthioalkyl, formyl, hydroxyl, CF$_3$, OCF$_3$, Het$_1$, O-alk-NH-cycloalkyl or SO$_2$NH$_2$, Het$_1$ represents a saturated or unsaturated and mono- or bicyclic heterocycle having 3 to 10 ring members and comprising one or more heteroatoms chosen from oxygen, sulfur and nitrogen and optionally substituted by one or more halogen, alkyl, alkoxy, alkoxycarbonyl, —CONR$_{22}$R$_{23}$, hydroxyl, hydroxyalkyl, oxo or SO$_2$NH$_2$, or B:

R represents a CHR$_{33}$ radical, $R_{33}$ represents an —NHCOR$_{34}$ or —N(R$_{35}$)—Y—R$_{36}$ radical, Y is CO or SO$_2$, $R_3$ and $R_4$, which are identical or different, represent either an aromatic radical chosen from phenyl, naphthyl and indenyl, these aromatic radicals being unsubstituted or substituted by one or more halogen, alkyl, alkoxy, formyl, hydroxyl, trifluoromethyl, trifluoromethoxy, —CO-alk, cyano, —COOH, —COOalk, —CONR$_{37}$R$_{38}$, —CO—NH—NR$_{39}$R$_{40}$, alkylsulfanyl, alkylsulfinyl, alkylsulfonyl, alkylsulfanylalkyl, alkylsulfinylalkyl, alkylsulfonylalkyl, hydroxyalkyl or -alk-NR$_{37}$R$_{38}$; or a heteroaromatic radical chosen from the benzofuryl, benzothiazolyl, benzothienyl, benzoxazolyl, chromanyl, 2,3-dihydrobenzofuryl, 2,3-dihydrobenzothienyl, pyrimidinyl, furyl, imidazolyl, isochromanyl, isoquinolyl, pyrrolyl, pyridyl, quinolyl, 1,2,3,4-tetrahydroisoquinolyl, thiazolyl and thienyl rings, it being possible for these heteroaromatic radicals to be unsubstituted or substituted by a halogen, alkyl, alkoxy, hydroxyl, trifluoromethyl, trifluoromethoxy, cyano, —COOH, —COOalk, —CO—NH—NR$_{39}$R$_{40}$, —CONR$_{37}$R$_{38}$, -alk-NR$_{39}$R$_{40}$, alkylsulfanyl, alkylsulfinyl, alkylsulfonyl, alkylsulfanylalkyl, alkylsulfinylalkyl, alkylsulfonylalkyl or hydroxyalkyl, R$_{34}$ represents an -alk-SO$_2$—R$_{41}$ radical, an -alk-SO$_2$—CH=CH—R$_{41}$ radical, a Het$_2$ radical substituted by —SO$_2$—R$_{41}$ or a phenyl radical substituted by —SO$_2$—R$_{41}$ or -alk-SO$_2$—R$_{41}$, R$_{35}$ represents a hydrogen atom or an alkyl radical, R$_{36}$ represents a phenylalkyl, Het$_2$ or Ar$_2$ radical, R$_{37}$ and R$_{38}$, which are identical or different, represent a hydrogen atom or an alkyl radical or else R$_{37}$ and R$_{38}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, R$_{39}$ and R$_{40}$, which are identical or different, represent a hydrogen atom or an alkyl, —COOalk, cycloalkyl, alkylcycloalkyl, -alk-O-alk or hydroxyalkyl radical or else R$_{39}$ and R$_{40}$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$, R$_{41}$ represents an alkyl, Ar$_2$ or Het$_2$ radical, Ar$_2$ represents a phenyl, naphthyl or indenyl radical, these radicals optionally being substituted by one or more halogen, alkyl, alkoxy, cyano, —CO-alk, —COOH, —COOalk, —CONR$_{42}$R$_{43}$, —CO—NH—NR$_{44}$R$_{45}$, alkylsulfanyl, alkylsulfinyl, alkylsulfonyl, -alk-NR$_{44}$R$_{45}$, —NR$_{44}$R$_{45}$, alkylthioalkyl, formyl, hydroxyl, hydroxyalkyl, Het$_2$, —O-alk-NH-cycloalkyl, OCF$_3$, CF$_3$, —NH—CO-alk, —SO$_2$NH$_2$, —HN—COCH$_3$, —NH—COOalk or Het$_2$ or else on two adjacent carbon atoms by a dioxymethylene, Het$_2$ represents a saturated or unsaturated and mono- or bicyclic heterocycle having 3 to 10 ring members and comprising one or more heteroatoms chosen from oxygen, sulfur and nitrogen optionally substituted by one or more alkyl, alkoxy, vinyl, halogen, alkoxycarbonyl, oxo, hydroxyl, OCF$_3$ or CF$_3$, the nitrogenous heterocycles optionally being in their N-oxidized form, R$_{42}$ and R$_{43}$, which are identical or different, represent a hydrogen atom or an alkyl radical or else R$_{42}$ and R$_{43}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl radicals, R$_{44}$ and R$_{45}$, which are identical or different, represent a hydrogen atom or an alkyl, —COOalk, cycloalkyl, alkylcycloalkyl, -alk-O-alk or hydroxyalkyl radical or else R$_{44}$ and R$_{45}$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$ radicals, or C:

R represents a CHR$_{46}$ radical,

R$_{46}$ represents an —N(R$_{47}$)R$_{48}$, —N(R$_{47}$)—CO—R$_{48}$ or —N(R$_{47}$)—SO$_2$R$_{49}$ radical, R$_3$ and R$_4$, which are identical or different, represent either an aromatic radical chosen from phenyl, naphthyl and indenyl, these aromatic radicals being unsubstituted or substituted by one or more halogen, alkyl, alkoxy, formyl, hydroxyl, trifluoromethyl, trifluoromethoxy, —CO-alk, cyano, —COOH, —COOalk, —CONR$_{50}$R$_{51}$, —CO—NH—NR$_{52}$R$_{53}$, alkylsulfanyl, alkylsulfinyl, alkylsulfonyl, alkylsulfanylalkyl, alkylsulfinylalkyl, alkylsulfonylalkyl, hydroxyalkyl or -alk-NR$_7$R$_8$ radicals; or a heteroaromatic radical chosen from the benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, it being possible for these heteroaromatic radicals to be unsubstituted or substituted by a halogen, alkyl, alkoxy, hydroxyl, trifluoromethyl, trifluoromethoxy, cyano, —COOH, —COOalk, —CO—NH—NR$_{52}$R$_{53}$, —CONR$_{50}$R$_{51}$, -alk-NR$_{52}$R$_{53}$, alkylsulfanyl, alkylsulfinyl, alkylsulfonyl, alkylsulfanylalkyl, alkylsulfinylalkyl, alkylsulfonylalkyl or hydroxyalkyl radical, R$_{47}$ represents a —C(R$_{54}$)(R$_{55}$)-Het$_3$, -Het$_3$, —C(R$_{54}$)(R$_{55}$)—Ar$_3$, Ar$_3$, cycloalkyl or norbornyl radical, R$_{48}$ represents a hydrogen atom or a hydroxyalkyl radical, -alk-COOalk radical, -alk-CONR$_{50}$R$_{51}$ radical, -alk-NR$_{50}$R$_5$, radical, alkoxy radical, Ar$_3$ radical, Het$_3$ radical, —CH$_2$Ar$_3$ radical, —CH$_2$Het$_3$ radical or alkyl radical optionally substituted with one or more halogen, R$_{49}$ represents a hydroxyalkyl radical, -alk-COOalk radical, -alk-CONR$_{50}$R$_5$, radical, -alk-NR$_{50}$R$_{51}$ radical, alkoxy radical, Ar$_3$ radical, Het$_3$ radical, —CH$_2$Ar$_3$ radical, —CH$_2$Het$_3$ radical or alkyl radical optionally substituted with one or more halogen, R$_{50}$ and R$_{51}$, which are identical or different, represent a hydrogen atom or an alkyl radical or else R$_{50}$ and R$_{51}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, R$_{52}$ and R$_{53}$, which are identical or different, represent a hydrogen atom or an alkyl, —COOalk, cycloalkyl, alkylcycloalkyl, -alk-O-alk or hydroxyalkyl radical or else R$_{52}$ and R$_{53}$ form, together with the nitrogen atom to which they are attached, a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$, R$_{54}$ represents a hydrogen atom or a hydroxyalkyl radical, -alk-COOalk radical, -alk-CONR$_{50}$R$_{51}$ radical, -alk-NR$_{50}$R$_5$, radical, alkoxyalkyl radical, Ar$_3$ radical, Het$_3$ radical, —CH$_2$Ar$_3$ radical, —CH$_2$Het$_3$ radical or alkyl radical optionally substituted with one or more halogen, R$_{55}$ represents a hydrogen atom or a hydroxyalkyl radical, -alk-COOalk radical, -alk-CONR$_{50}$R$_{51}$ radical, -alk-NR$_{50}$R$_5$, radical, alkoxyalkyl radical or alkyl radical optionally substituted with one or more halogen, or else R$_{54}$ and R$_{55}$ form, together with the carbon atom to which they are attached, a saturated mono- or bicyclic ring having 3 to 10 ring members optionally comprising another heteroatom chosen from oxygen, sulfur and nitrogen and optionally being substituted by one or more alkyl, Ar$_3$ represents a phenyl, naphthyl or indenyl radical, these various radicals optionally being substituted by one or more halogen, alkyl, alkoxy, —CO-alk, cyano, —COOH, —COOalk, —CONR$_{56}$R$_{57}$, —CO—NH—NR$_{58}$R$_{59}$, alkylsulfanyl, alkylsulfinyl, alkylsulfonyl, -alk-NR$_{58}$R$_{59}$, —NR$_{58}$R$_{59}$, alkylthioalkyl, formyl, CF$_3$, OCF$_3$, Het$_3$, —O-alk-NH-cycloalkyl, SO$_2$NH$_2$, hydroxyl, hydroxyalkyl, —NHCOalk or —NHCOOalk or on 2 adjacent carbon atoms by dioxymethylene, Het$_3$ represents a saturated or unsaturated and mono- or bicyclic heterocycle having 3 to 10 ring members and comprising one or more heteroatoms chosen from oxygen, sulfur and nitrogen optionally substituted by one or more alkyl, alkoxy, halogen, alkoxycarbonyl, oxo or hydroxyl, the nitrogenous heterocycles optionally being in their N-oxidized form, R$_{56}$ and R$_{57}$, which are identical or different, represent a hydrogen atom or an alkyl radical or else R$_{56}$ and R$_{57}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, R$_{58}$ and R$_{59}$, which are identical or different, represent a hydrogen atom or an alkyl radical or else R$_{58}$ and R$_{59}$ form, together with the nitrogen atom to which they are attached, a saturated mono- or bicyclic heterocycle having 3 to 10 ring members optionally comprising another heteroatom chosen from oxygen, sulfur and nitrogen and optionally being substituted by one or more alkyl, alk represents an alkyl or alkylene radical, the alkyl and alkylene radicals as well as the alkoxy radicals may feature straight or branched chains and comprise 1 to 6 carbon atoms, the cycloalkyl radicals comprise 3 to 10 carbon atoms and the heterocycloalkyl and heterocyclenyl radicals comprise 3 to 10 carbon atoms, the optical isomers of these compounds and their pharmaceutically acceptable salts with an inorganic or organic acid.

Mention may be made, among preferred azetidine derivatives which are a subject-matter of the present invention, of the following derivatives:

(RS)-1-[bis(4-chlorophenyl)methyl)]-3-[(3,5-difluorophenyl)(methylsulfonyl)methyl]azetidine,
(R)-1-[bis(4-chlorophenyl)methyl)]-3-[(3,5-difluorophenyl)(methylsulfonyl)methyl]azetidine,
(S)-1-[bis(4-chlorophenyl)methyl)]-3-[(3,5-difluorophenyl)(methylsulfonyl)methyl]azetidine,
(RS)-1-[bis(4-chlorophenyl)methyl)]-3-[(pyrid-3-yl)-(methylsulfonyl)methyl]azetidine,
(R)-1-[bis(4-chlorophenyl)methyl)]-3-[(pyrid-3-yl)-(methylsulfonyl)methyl]azetidine,
(S)-1-[bis(4-chlorophenyl)methyl)]-3-[(pyrid-3-yl)-(methylsulfonyl)methyl]azetidine,
(RS)-1-[bis(3-fluorophenyl)methyl]-3-[(3,5-difluorophenyl)(methylsulfonyl)methyl]azetidine,
(R)-1-[bis(3-fluorophenyl)methyl]-3-[(3,5-difluorophenyl)(methylsulfonyl)methyl]azetidine,
(S)-1-[bis(3-fluorophenyl)methyl]-3-[(3,5-difluorophenyl)(methylsulfonyl)methyl]azetidine,
1-[bis(4-chlorophenyl)methyl]-3-(RS)-{[3-(azetidin-1-yl)phenyl](methylsulfonyl)methyl}azetidine,
1-[bis(4-chlorophenyl)methyl]-3-(R)-{[3-(azetidin-1-yl)phenyl](methylsulfonyl)methyl}azetidine,
1-[bis(4-chlorophenyl)methyl]-3-(S)-{[3-(azetidin-1-yl)phenyl](methylsulfonyl)methyl}azetidine,
(RS)-1-[3-({1-[bis(4-chlorophenyl)methyl]azetidin-3-yl}(methylsulfonyl)methyl)phenyl]pyrrolidine,
(R)-1-[3-({1-[bis(4-chlorophenyl)methyl]azetidin-3-yl}(methylsulfonyl)methyl)phenyl]pyrrolidine,
(S)-1-[3-({1-[bis(4-chlorophenyl)methyl]azetidin-3-yl}(methylsulfonyl)methyl)phenyl]pyrrolidine,
(RS)—N-[3-({1-[bis(4-chlorophenyl)methyl]azetidin-3-yl}(methylsulfonyl)methyl)phenyl]-N-methylamine,
(R)—N-[3-({1-[bis(4-chlorophenyl)methyl]azetidin-3-yl}(methylsulfonyl)methyl)phenyl]-N-methylamine,
(S)—N-[3-({1-[bis(4-chlorophenyl)methyl]azetidin-3-yl}(methylsulfonyl)methyl)phenyl]-N-methylamine,
(RS)-1-[bis(4-chlorophenyl)methyl]-3-[(3,5-bis(trifluoromethyl)phenyl)(methylsulfonyl)methyl]azetidine,
(R)-1-[bis(4-chlorophenyl)methyl]-3-[(3,5-bis(trifluoromethyl)phenyl)(methylsulfonyl)methyl]azetidine,
(S)-1-[bis(4-chlorophenyl)methyl]-3-[(3,5-bis(trifluoromethyl)phenyl)(methylsulfonyl)methyl]azetidine,
1-[bis(4-chlorophenyl)methyl]-3-(phenylsulfonylmethyl)azetidine,
(RS)-1-[bis(4-chlorophenyl)methyl]-3-[(3,5-difluorophenyl)(methylsulfonyl)methyl]-3-methylazetidine,
(R)-1-[bis(4-chlorophenyl)methyl]-3-[(3,5-difluorophenyl)methylsulfonylmethyl]-3-methylazetidine,
(S)-1-[bis(4-chlorophenyl)methyl]-3-[(3,5-difluorophenyl)(methylsulfonyl)methyl]-3-methylazetidine,
(RS)-2-{1-[bis(4-chlorophenyl)methyl]azetidin-3-yl}-2-(3,5-difluorophenyl)-N-cyclohexylacetamide,
(R)-2-{1-[bis(4-chlorophenyl)methyl]azetidin-3-yl}-2-(3,5-difluorophenyl)-N-cyclohexylacetamide,
(S)-2-{1-[bis(4-chlorophenyl)methyl]azetidin-3-yl}-2-(3,5-difluorophenyl)-N-cyclohexylacetamide,
(RS)-2-{1-[bis(4-chlorophenyl)methyl]azetidin-3-yl}-2-(3,5-difluorophenyl)-N-isobutylacetamide,
(R)-2-{1-[bis(4-chlorophenyl)methyl]azetidin-3-yl}-2-(3,5-difluorophenyl)-N-isobutylacetamide,
(S)-2-{1-[bis(4-chlorophenyl)methyl]azetidin-3-yl}-2-(3,5-difluorophenyl)-N-isobutylacetamide,
(RS)-2-{1-[bis(4-chlorophenyl)methyl]azetidin-3-yl}-2-(3,5-difluorophenyl)-N-cyclopropylmethylacetamide,
(R)-2-{1-[bis(4-chlorophenyl)methyl]azetidin-3-yl}-2-(3,5-difluorophenyl)-N-isopropylacetamide,
(S)-2-{1-[bis(4-chlorophenyl)methyl]azetidin-3-yl}-2-(3,5-difluorophenyl)-N-cyclopropylmethylacetamide,
(RS)-2-{1-[bis(4-chlorophenyl)methyl]azetidin-3-yl}-2-(3,5-difluorophenyl)-N-isopropylacetamide,
(R)-2-{1-[bis(4-chlorophenyl)methyl]azetidin-3-yl}-2-(3,5-difluorophenyl)-N-isopropylacetamide,
(S)-2-{1-[bis(4-chlorophenyl)methyl]azetidin-3-yl}-2-(3,5-difluorophenyl)-N-isopropylacetamide,
(RS)-1-[bis(4-chlorophenyl)methyl]-3-[1-(3,5-difluorophenyl)-1-(methylsulfonyl)ethyl]azetidine,
(R)-1-[bis(4-chlorophenyl)methyl]-3-[1-(3,5-difluorophenyl)-1-(methylsulfonyl)ethyl]azetidine,
(S)-1-[bis(4-chlorophenyl)methyl]-3-[1-(3,5-difluorophenyl)-1-(methylsulfonyl)ethyl]azetidine,
(RS)-1-[bis(4-fluorophenyl)methyl]-3-[(3,5-difluorophenyl)(methylsulfonyl)methyl]azetidine,
(R)-1-[bis(4-fluorophenyl)methyl]-3-[(3,5-difluorophenyl)(methylsulfonyl)methyl]azetidine,
(S)-1-[bis(4-fluorophenyl)methyl]-3-[(3,5-difluorophenyl)(methylsulfonyl)methyl]azetidine,
(RS)-{1-[(3-pyridyl)(4-chlorophenyl)methyl]-3-[(3,5-difluorophenyl)(methylsulfonyl)methyl]azetidine, (SS)-{1-[(3-pyridyl)(4-chlorophenyl)methyl]-3-[(3,5-difluorophenyl)(methylsulfonyl)methyl]azetidine,
(RR)-{1-[(3-pyridyl)(4-chlorophenyl)methyl]-3-[(3,5-difluorophenyl)(methylsulfonyl)methyl]azetidine,
(SR)-{1-[(3-pyridyl)(4-chlorophenyl)methyl]-3-[(3,5-difluorophenyl)(methylsulfonyl)methyl]azetidine,
(RS)-{1-[(4-pyridyl)(4-chlorophenyl)methyl]-3-[(3,5-difluorophenyl)(methylsulfonyl)methyl]azetidine,
(SS)-{1-[(4-pyridyl)(4-chlorophenyl)methyl]-3-[(3,5-difluorophenyl)(methylsulfonyl)methyl]azetidine,
(RR)-{1-[(4-pyridyl)(4-chlorophenyl)methyl]-3-[(3,5-difluorophenyl)(methylsulfonyl)methyl]azetidine,
(SR)-{1-[(4-pyridyl)(4-chlorophenyl)methyl]-3-[(3,5-difluorophenyl)(methylsulfonyl)methyl]azetidine,
(RS)-5-((4-chlorophenyl){3-[(3,5-difluorophenyl)-(methylsulfonyl)methyl]azetidin-1-yl}methyl)pyrimidine,
(SR)-5-((4-chlorophenyl){3-[(3,5-difluorophenyl)-(methylsulfonyl)methyl]azetidin-1-yl}methyl)pyrimidine,
(RR)-5-((4-chlorophenyl){3-[(3,5-difluorophenyl)-(methylsulfonyl)methyl]azetidin-1-yl}methyl)pyrimidine,
(SS)-5-((4-chlorophenyl){3-[(3,5-difluorophenyl)-(methylsulfonyl)methyl]azetidin-1-yl}methyl)pyrimidine,
(SS)-{1-[(2-chloropyrid-5-yl)(4-chlorophenyl)methyl]-3-[(3,5-difluorophenyl)(methylsulfonyl)methyl]azetidine,
(RR)-{1-[(2-chloropyrid-5-yl)(4-chlorophenyl)methyl]-3-[(3,5-difluorophenyl)(methylsulfonyl)methyl]azetidine,
(RS)-{1-[(2-chloropyrid-5-yl)(4-chlorophenyl)methyl]-3-[(3,5-difluorophenyl)(methylsulfonyl)methyl]azetidine,
(SR)-{1-[(2-chloropyrid-5-yl)(4-chlorophenyl)methyl]-3-[(3,5-difluorophenyl)(methylsulfonyl)methyl]azetidine,
N-{1-[bis(4-chlorophenyl)methyl]azetidin-3-yl}thien-2-ylsulfonamide,
N-{1-[bis(4-chlorophenyl)methyl]azetidin-3-yl}-4-methoxyphenylsulfonamide,
N-[4-(N-{1-[bis(4-chlorophenyl)methyl]azetidin-3-yl}sulfamoyl)phenyl]acetamide,
N-{1-[bis(4-chlorophenyl)methyl]azetidin-3-yl}-4-methylphenylsulfonamide,
N-{1-[bis(4-chlorophenyl)methyl]azetidin-3-yl}-3,4-dimethoxyphenylsulfonamide,
N-{1-[bis(4-chlorophenyl)methyl]azetidin-3-yl}-3-fluorophenylsulfonamide,
N-{1-[bis(4-chlorophenyl)methyl]azetidin-3-yl}-3,4-dichlorophenylsulfonamide,
N-{1-[bis(4-chlorophenyl)methyl]azetidin-3-yl}-3-cyanophenylsulfonamide,
N-{1-[bis(4-chlorophenyl)methyl]azetidin-3-yl}-2,5-dimethoxyphenylsulfonamide,
N-{1-[bis(4-chlorophenyl)methyl]azetidin-3-yl}-3-trifluoromethylphenylsulfonamide,
N-{1-[bis(4-chlorophenyl)methyl]azetidin-3-yl}naphth-2-ylsulfonamide,
N-{1-[bis(4-chlorophenyl)methyl]azetidin-3-yl}naphth-1-ylsulfonamide,
N-{1-[bis(4-chlorophenyl)methyl]azetidin-3-yl}-3,4-difluorophenylsulfonamide,
N-{1-[bis(4-chlorophenyl)methyl]azetidin-3-yl}-1-methyl-1H-imidazol-4-ylsulfonamide,
N-[4-(N-{1-[bis(4-chlorophenyl)methyl]azetidin-3-yl}sulfamoyl)-2-chlorophenyl]acetamide,
N-{1-[bis(4-chlorophenyl)methyl]azetidin-3-yl}pyrid-3-ylsulfonamide,
N-{1-[bis(4-chlorophenyl)methyl]azetidin-3-yl}-4-fluorophenylsulfonamide,
N-{1-[bis(4-chlorophenyl)methyl]azetidin-3-yl}quinol-8-ylsulfonamide,
N-{1-[bis(4-chlorophenyl)methyl]azetidin-3-yl}phenylsulfonamide,
N-{1-[bis(4-chlorophenyl)methyl]azetidin-3-yl}(phenylmethyl)sulfonamide,
N-{1-[bis(4-chlorophenyl)methyl]azetidin-3-yl}-3,5-difluorophenylsulfonamide,
N-{1-[bis(4-chlorophenyl)methyl]azetidin-3-yl}pyrid-2-ylsulfonamide,
N-{1-[bis(4-chlorophenyl)methyl]azetidin-3-yl}-(3-fluoro-5-pyrrolidin-1-ylphenyl)sulfonamide,
N-{1-[bis(4-chlorophenyl)methyl]azetidin-3-yl}-N-methyl-4-fluorophenylsulfonamide,
N-{1-[bis(4-chlorophenyl)methyl]azetidin-3-yl}-N-methylquinol-8-ylsulfonamide,
N-{1-[bis(4-chlorophenyl)methyl]azetidin-3-yl}-N-methylphenylsulfonamide,
N-{1-[bis(4-chlorophenyl)methyl]azetidin-3-yl}-N-methyl(phenylmethyl)sulfonamide,
N-{1-[bis(4-chlorophenyl)methyl]azetidin-3-yl}-3-sulfamoylphenylsulfonamide,
2-benzenesulfonyl-N-{1-[bis(4-chlorophenyl)methyl]-azetidin-3-yl}acetamide,
N-{1-[bis(4-chlorophenyl)methyl]azetidin-3-yl}-2-(toluene-4-sulfonyl)acetamide,
(3-chloro-4-(methylsulfonyl)thiophene-2-carboxy){1-[bis(4-chlorophenyl)methyl]azetidin-3-yl}amide,
N-{1-[bis(4-chlorophenyl)methyl]azetidin-3-yl}-3-(2-phenylethylenesulfonyl)propionamide,
N-{1-[bis(4-chlorophenyl)methyl]azetidin-3-yl}-4-(methylsulfonyl)benzamide,
(5-(methylsulfonyl)thiophene-2-carboxy)-{1-[bis(4-chlorophenyl)methyl]azetidin-3-yl}amide,
(5-(methylsulfonyl)-3-methyl-4-vinylthiophene-2-carboxy){1-[bis(4-chlorophenyl)methyl]azetidin-3-yl}amide,
(RS)—N-{1-[{4-chlorophenyl)(pyridin-3-yl)methyl]-azetidin-3-yl}-3,5-difluorobenzenesulfonamide,
(RS)—N-{1-[{4-chlorophenyl)(pyrimidin-5-yl)methyl]-azetidin-3-yl}-3,5-difluorobenzenesulfonamide,
N-{1-[bis{4-chlorophenyl)methyl]azetidin-3-yl}-N-(6-chloropyrid-2-yl)methylsulfonamide,
N-{1-[bis{4-chlorophenyl)methyl]azetidin-3-yl}-N-(6-ethylpyrid-2-yl)methylsulfonamide,
N-{1-[bis{4-chlorophenyl)methyl]azetidin-3-yl}-N-(quinol-6-yl)methylsulfonamide,
N-{1-[bis{4-chlorophenyl)methyl]azetidin-3-yl}-N-(quinol-5-yl)methylsulfonamide,
N-{1-[bis{4-chlorophenyl)methyl]azetidin-3-yl}-N-(isoquinol-5-yl)methylsulfonamide,
N-{1-[bis{4-chlorophenyl)methyl]azetidin-3-yl}-N-(pyrid-3-yl)methylsulfonamide,
N-{1-[bis{4-chlorophenyl)methyl]azetidin-3-yl}-N-(1-oxidopyrid-3-yl)methylsulfonamide,
N-((1R,2S,4S)bicyclo[2.2.1]hept-2-yl)-N-{1-[bis(4-chlorophenyl)methyl]azetidin-3-yl}methylsulfonamide,
N-((1R,2R,4S)bicyclo[2.2.1]hept-2-yl)-N-{1-[bis(4-chlorophenyl)methyl]azetidin-3-yl}methylsulfonamide,
N-{1-[bis(4-chlorophenyl)methyl]azetidin-3-yl}-N-(3,5-difluorophenyl)methylsulfonamide,
N-{1-[bis(4-chlorophenyl)methyl]azetidin-3-yl}-N-(thiazol-2-yl)methylsulfonamide,
N-{1-[bis(4-chlorophenyl)methyl]azetidin-3-yl}-N-(3-methoxyphenyl)methylsulfonamide,
N-{1-[bis(4-chlorophenyl)methyl]azetidin-3-yl}-N-(3-(hydroxyphenyl)methylsulfonamide,
N-{1-[bis(4-chlorophenyl)methyl]azetidin-3-yl}-N-(3-(hydroxymethyl)phenyl)methylsulfonamide, ethyl N-{1-[bis(4-chlorophenyl)methyl]azetidin-3-yl}-N-(methylsulfonyl)-3-aminobenzoate
N-{1-[bis(4-chlorophenyl)methyl]azetidin-3-yl}-N-(1-isobutylpiperid-4-yl)methylsulfonamide,
N-benzyl-N-{1-{bis(4-chlorophenyl)methyl]azetidin-3-yl}amine
N-{1-[bis(4-chlorophenyl)methyl]azetidin-3-yl}-N-(3,5-difluorobenzyl)amine,
N-{1-[bis(4-chlorophenyl)methyl]azetidin-3-yl}-N-(3,5-difluorobenzyl)methylsulfonamide,
N-{1-[bis(4-chlorophenyl)methyl]azetidin-3-yl}-N-(pyrid-3-ylmethyl)methylsulfonamide,
N-{1-[bis(4-fluorophenyl)methyl]azetidin-3-yl}-N-(3,5-difluorophenyl)methylsulfonamide,
(RS)—N-{1-[(4-chlorophenyl)(pyrid-3-yl)methyl]azetidin-3-yl}-N-(3,5-difluorophenyl)methylsulfonamide,
(R)—N-{1-[(4-chlorophenyl)(pyrid-3-yl)methyl]azetidin-3-yl}-N-(3,5-difluorophenyl)methylsulfonamide,
(S)—N-{1-[(4-chlorophenyl)(pyrid-3-yl)methyl]azetidin-3-yl}-N-(3,5-difluorophenyl)methylsulfonamide,
(RS)—N-{1-[(4-chlorophenyl)(pyrid-4-yl)methyl]azetidin-3-yl}-N-(3,5-difluorophenyl)methylsulfonamide,
(R)—N-{1-[(4-chlorophenyl)(pyrid-4-yl)methyl]azetidin-3-yl}-N-(3,5-difluorophenyl)methylsulfonamide,
(S)—N-{1-[(4-chlorophenyl)(pyrid-4-yl)methyl]azetidin-3-yl}-N-(3,5-difluorophenyl)methylsulfonamide,
(RS)—N-{1-[(4-chlorophenyl)(pyrimidin-5-yl)methyl]-azetidin-3-yl}-N-(3,5-difluorophenyl)methylsulfonamide,
(R)—N-{1-[(4-chlorophenyl)(pyrimidin-5-yl)methyl]-azetidin-3-yl}-N-(3,5-difluorophenyl)methylsulfonamide,
(S)—N-{1-[(4-chlorophenyl)(pyrimidin-5-yl)methyl]-azetidin-3-yl}-N-(3,5-difluorophenyl)methylsulfonamide,
N-{1-[bis(4-chlorophenyl)methyl]azetidin-3-yl}-N-(3,5-difluorophenyl)benzylsulfonamide, their optical isomers and their pharmaceutically acceptable salts.

Mention may be made, as examples of pharmaceutically acceptable salts of azetidine derivatives, of the following salts: benzenesulfonate, hydrobromide, hydrochloride, citrate, ethanesulfonate, fumarate, gluconate, iodate, isethionate, maleate, methanesulfonate, methylenebis(oxynaphthoate), nitrate, oxalate, pamoate, phosphate, salicylate, succinate, sulfate, tartrate, theophyllineacetate and p-toluenesulfonate.

The azetidine derivatives are synthesized according to the following general methods:

The compounds of formula (I) for which R represents the $CR_1R_2$ radical in which $R_1$ represents a hydrogen atom and $R_2$ represents a $C(R_8)$ $(R_{11})$ $(R_{12})$ radical in which $R_8$ represents a hydrogen atom, $R_{11}$ represents an —$SO_2$—$Ar_1$, —$SO_2$-$Het_1$ or —$SO_2$alk radical and $R_{12}$ represents a hydrogen atom or an $Ar_1$ or $Het_1$ radical and the compounds of formula (I) for which R represents a $C=C(R_5)SO_2R_6$ or $C=C(R_7)SO_2$alk radical can be prepared according to the following reaction scheme:

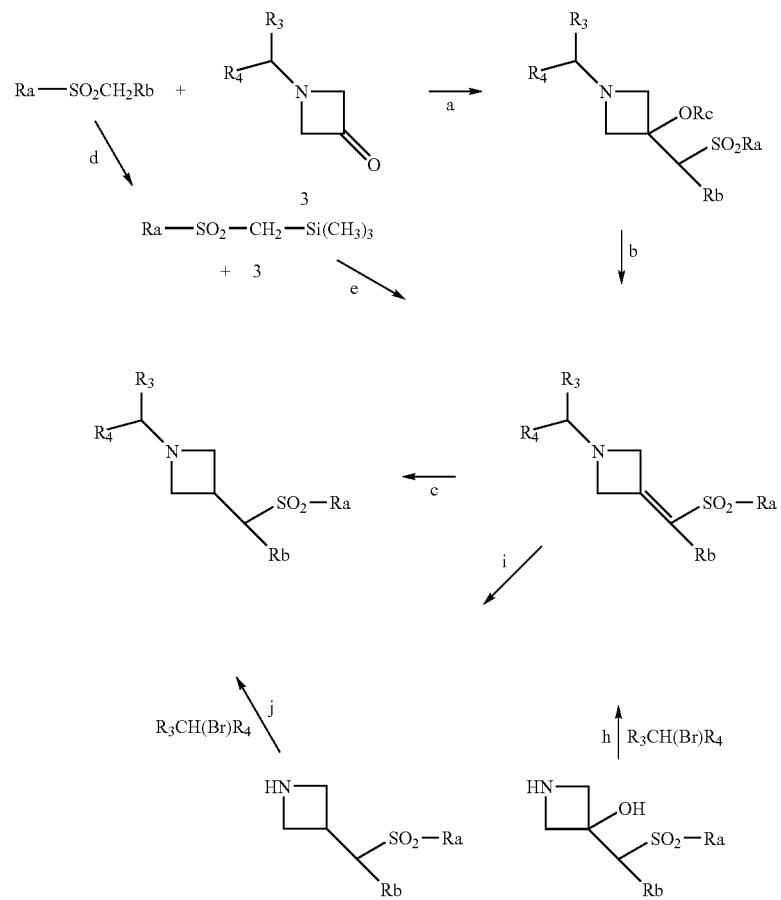

-continued

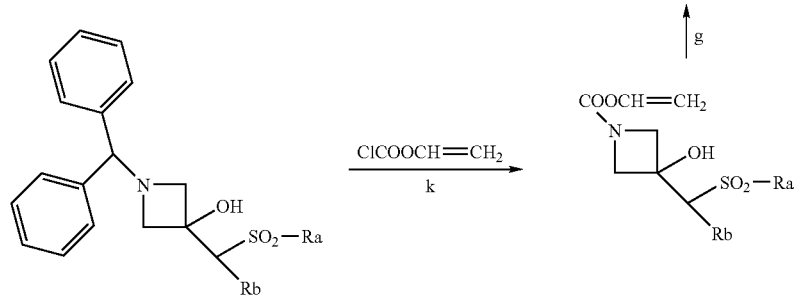

In these formulae, either Ra represents an alkyl, $Het_1$ or $Ar_1$ radical and Rb represents a hydrogen atom or an $Ar_1$ or $Het_1$ radical; or Ra represents an $Ar_1$ or $Het_1$ radical and Rb represents a hydrogen atom or an alkyl radical; or Ra represents an alkyl radical and Rb represents a cycloalkyl, heterocycloalkyl or heterocyclenyl radical optionally substituted by a —CSO-phenyl radical; and Rc represents a hydrogen atom or an acetyl radical; $R_3$, $R_4$, $Ar_1$ and $Het_1$ have the same meanings as in the formula (I).

The reactions d and e can only be used when Rb is a hydrogen atom.

The reaction a is generally carried out in an inert solvent, such as an ether (for example tetrahydrofuran), in the presence of a strong base, such as tert-butyllithium, n-butyllithium, lithium diisopropylamide or potassium tert-butoxide, at a temperature of between −70° C. and −15° C.

The dehydration reaction b is generally carried out by any dehydration method known to a person skilled in the art which makes it possible to dehydrate an alcohol to produce the corresponding alkene. Preferably, the acetyloxy derivative is prepared by reaction with acetyl chloride in an inert solvent, such as pyridine, tetrahydrofuran, dioxane or a chlorinated solvent (for example dichloromethane or chloroform), at a temperature of between 5° C. and 20° C., and then the product is treated with a base, such as an alkali metal hydroxide (for example sodium hydroxide), an alkali metal carbonate (for example sodium carbonate or potassium carbonate) or an amine, such as a trialkylamine (for example triethylamine), 4-dimethylaminopyridine or 1,8-diazabicyclo[5.4.0]undec-7-ene, at a temperature of between 0° C. and the boiling temperature of the reaction medium. The intermediate acetyloxy may or may not be isolated. The acetyloxy can also be prepared directly in the reaction medium of reaction a.

The reduction c is generally carried out in an inert solvent, such as a (1-4C) aliphatic alcohol (for example methanol), a chlorinated solvent (for example chloroform or dichloromethane) or a mixture of these solvents, in the presence of $NaBH_4$, at a temperature of between 0° C. and the boiling temperature of the reaction medium.

The reaction d is carried out by reaction with trimethylsilyl chloride in an inert solvent, such as an ether (for example tetrahydrofuran), in the presence of n-butyllithium, at a temperature of −70° C.

The reaction e is generally carried out in an inert solvent, such as an ether (for example tetrahydrofuran), in the presence of a strong base, such as tert-butyllithium, n-butyllithium, lithium diisopropylamide or potassium tert-butoxide, at a temperature of between −70° C. and −15° C.

The hydrolysis g is carried out in an inert solvent, such as an ether (for example dioxane), by means of hydrochloric acid at a temperature in the region of 20° C.

The reactions h and j are preferably carried out in an inert solvent, such as acetonitrile, in the presence of a base, such as an alkali metal carbonate (for example potassium carbonate), at the boiling temperature of the reaction medium.

The reaction i is carried out under a hydrogen atmosphere in the presence of a catalyst, such as palladium or one of its derivatives, in an inert solvent, such as methanol or ethanol, at a temperature of between 15° C. and 60° C.

The reaction k is carried out in an inert solvent, such as a chlorinated solvent (for example dichloromethane or chloroform), at a temperature of between 0° C. and the boiling temperature of the reaction mixture.

The $R_3CH(Br)R_4$ derivatives are commercially available or can be obtained by application or adaptation of the method described by Bachmann W. E., J. Am. Chem. Soc., 2135 (1933). Generally, the corresponding alcohol $R_3CHOHR_4$ is brominated by means of hydrobromic acid in acetic acid at a temperature of between 0° C. and the boiling temperature of the reaction medium.

The corresponding alcohols $R_3CHOHR_4$ are commercially available or can be obtained by application or adaptation of the methods described by Plasz A. C. et al., J. Chem. Soc. Chem. Comm., 527 (1972).

The following intermediates can be obtained by application or adaptation of the methods described in the examples. The following reaction schemes in particular are used:

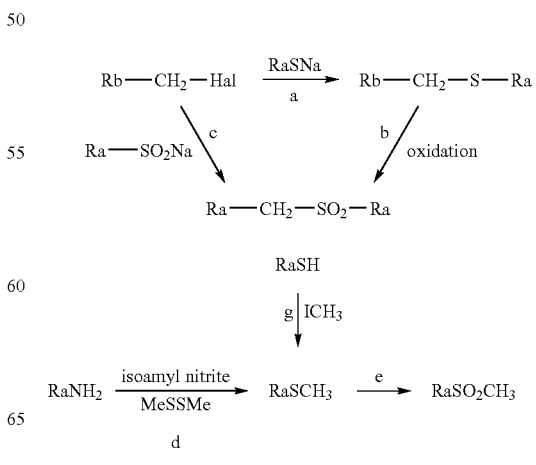

-continued

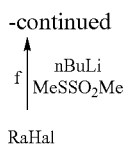

In these formulae, Hal represents a halogen atom and preferably chlorine, bromine or iodine.

The reaction is generally carried out in an inert solvent, such as dimethylformamide or a 1-4C aliphatic alcohol, at a temperature of between 20° C. and 30° C.

The reactions b and e are carried out by any known method which makes it possible to oxidize a sulfur derivative without affecting the remainder of the molecule, such as those described by M. Hudlicky, Oxidations in Organic Chemistry, ACS Monograph, 186, 252–263 (1990). For example, the reaction is carried out by the action of an organic peroxyacid or a salt of such a peroxyacid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or inorganic peracids or a salt of such an acid (for example periodic or persulfuric acid) in an inert solvent, such as a chlorinated solvent (for example chloroform and dichloromethane), at a temperature of between 0 and 25° C. Use may also be made of hydrogen peroxide, optionally in the presence of a metal oxide (sodium tungstate) or a periodate (for example sodium periodate), in an inert solvent, such as a 1-4C aliphatic alcohol (for example methanol or ethanol), acetic acid, water or a mixture of these solvents, at a temperature of between 0 and 60° C. It is also possible to carry out the reaction by means of tert-butyl hydroperoxide in the presence of titanium tetraisopropylate in a 1-4C aliphatic alcohol (for example methanol or ethanol) or a water/alcohol mixture, at a temperature in the region of 25° C., or by means of oxone$^R$ (potassium peroxymonosulfate) in a 1-4C aliphatic alcohol (for example methanol or ethanol), in the presence of water, acetic acid or sulfuric acid, at a temperature in the region of 20° C.

The reaction c is preferably carried out in an inert solvent, such as a 1-4C aliphatic alcohol (for example methanol or ethanol), at a temperature of between 20° C. and the boiling temperature of the reaction medium.

The reaction d is carried out under an inert atmosphere (argon) at a temperature of between 50° C. and the boiling temperature of the reaction medium.

The reaction f is generally carried out in an inert solvent, such as tetrahydrofuran or an aliphatic ether (for example ethyl ether), at a temperature in the region of −70° C.

The reaction g is generally carried out in an inert solvent, such as dimethylformamide, an aliphatic ether (for example ethyl ether) or a 1-4 aliphatic alcohol, in the presence of a base (for example sodium hydride), at a temperature of between 0° C. and 60° C.

The derivatives of formula Rb—CH$_2$-Hal are commercially available or can be obtained by application or adaptation of the methods described in the examples. In particular, the corresponding methyl derivative or alcohol is halogenated by means of a halogenating agent, such as hydrobromic acid in acetic acid at a temperature in the region of 20° C. or N-bromo- or N-chlorosuccinimide in the presence of benzoyl peroxide in an inert solvent, such as tetrachloromethane, at the boiling temperature of the reaction medium. The corresponding methyl derivatives or alcohols are commercially available or can be obtained according to the methods described by Brine G. A. et al., J. Heterocycl. Chem., 26, 677 (1989), and Nagarathnam D., Synthesis, 8, 743 (1992), and in the examples.

The azetidinones of formula 3 can be obtained by application or adaptation of the methods described by Katritzky A. R. et al., J. Heterocycl. Chem., 271 (1994), or Dave P. R., J. Org. Chem., 61, 5453 (1996), and in the examples. The preparations are generally carried out according to the following reaction scheme:

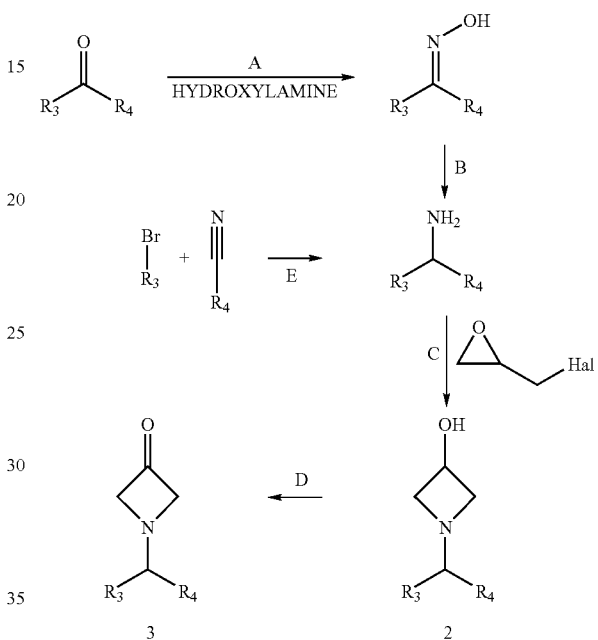

In these formulae, R$_3$ and R$_4$ have the same meanings as in formula (I) and Hal represents a chlorine or bromine atom.

In stage A, the reaction is preferably carried out in an inert solvent, such as a 1-4C aliphatic alcohol (for example ethanol or methanol), optionally in the presence of an alkali metal hydroxide, at the boiling temperature of the reaction medium.

In stage B, the reduction is generally carried out by means of lithium aluminum hydride in tetrahydrofuran at the boiling temperature of the reaction medium.

In stage C, the reaction is preferably carried out in an inert solvent, such as a 1-4C aliphatic alcohol (for example ethanol or methanol), in the presence of sodium hydrogencarbonate at a temperature of between 20° C. and the boiling temperature of the reaction medium.

In stage D, the oxidation is carried out preferably in DMSO by means of the sulfur trioxide-pyridine complex at a temperature in the region of 20° C. or by means of dimethyl sulfoxide, in the presence of oxalyl chloride and of triethylamine, at a temperature of between −70 and −50° C.

In stage E, the reaction is carried out according to the method described by Grisar M. et al., in J. Med. Chem., 885 (1973). The magnesium product of the bromine derivative is formed and then the nitrile is reacted in an ether, such as ethyl ether, at a temperature of between 0° C. and the boiling temperature of the reaction medium. After hydrolysis with an alcohol, the intermediate imine is reduced in situ with sodium borohydride at a temperature of between 0° C. and the boiling temperature of the reaction medium.

The $R_3$—CO—$R_4$ derivatives are commercially available or can be obtained by application or adaptation of the methods described by Kunder N. G. et. al., J. Chem. Soc. Perkin Trans. 1, 2815 (1997); Moreno-Marras M., Eur. J. Med. Chem., 23 (5), 477 (1988); Skinner et al., J. Med. Chem., 14 (6), 546 (1971); Hurn N. K., Tet. Lett., 36 (52), 9453 (1995); Medici A. et al., Tet. Lett, 24 (28), 2901 (1983); Riecke R. D. et al., J. Org. Chem., 62 (20), 6921 (1997); Knabe J. et al., Arch. Pharm., 306 (9), 648 (1973); Consonni R. et al., J. Chem. Soc. Perkin Trans. 1, 1809 (1996); FR-96-2481 and JP-94-261393; all of the references described herein are incorporated herein by reference in their entirety.

The $R_3$Br derivatives are commercially available or can be obtained by application or adaptation of the methods described by Brandsma L. et al., Synth. Comm., 20 (11), 1697 and 3153 (1990); Lemaire M. et al., Synth. Comm., 24 (1), 95 (1994); Goda H. et al., Synthesis, 9, 849 (1992); and Baeuerle P. et al., J. Chem. Soc. Perki Trans. 2, 489 (1993); all of the references described herein are incorporated herein by reference in their entirety.

The $R_4$CN derivatives are commercially available or can be obtained by application or adaptation of the methods described by Bouyssou P. et al., J. Het. Chem., 29 (4), 895 (1992); Suzuki N. et al., J. Chem. Soc. Chem. Comm., 1523 (1984); Marburg S. et al., J. Het. Chem., 17, 1333 (1980); and Percec V. et al., J. Org. Chem., 60 (21), 6895 (1995); all of the references described herein are incorporated herein by reference in their entirety.

The compounds of formula (I) for which R represents a $CR_1R_2$ radical in which $R_1$ represents a hydrogen atom and $R_2$ represents a $C(R_8)$ $(R_9)$ $(R_{10})$ radical in which $R_8$ represents a hydrogen atom, $R_9$ represents a —CO—$NR_{26}R_{27}$, —COOH, —COOalk, —$CH_2$OH, —NHCOOalk or —NH—CO—NH-alk radical and $R_{10}$ represents an $Ar_1$ or $Het_1$ radical can be prepared according to the following reaction scheme:

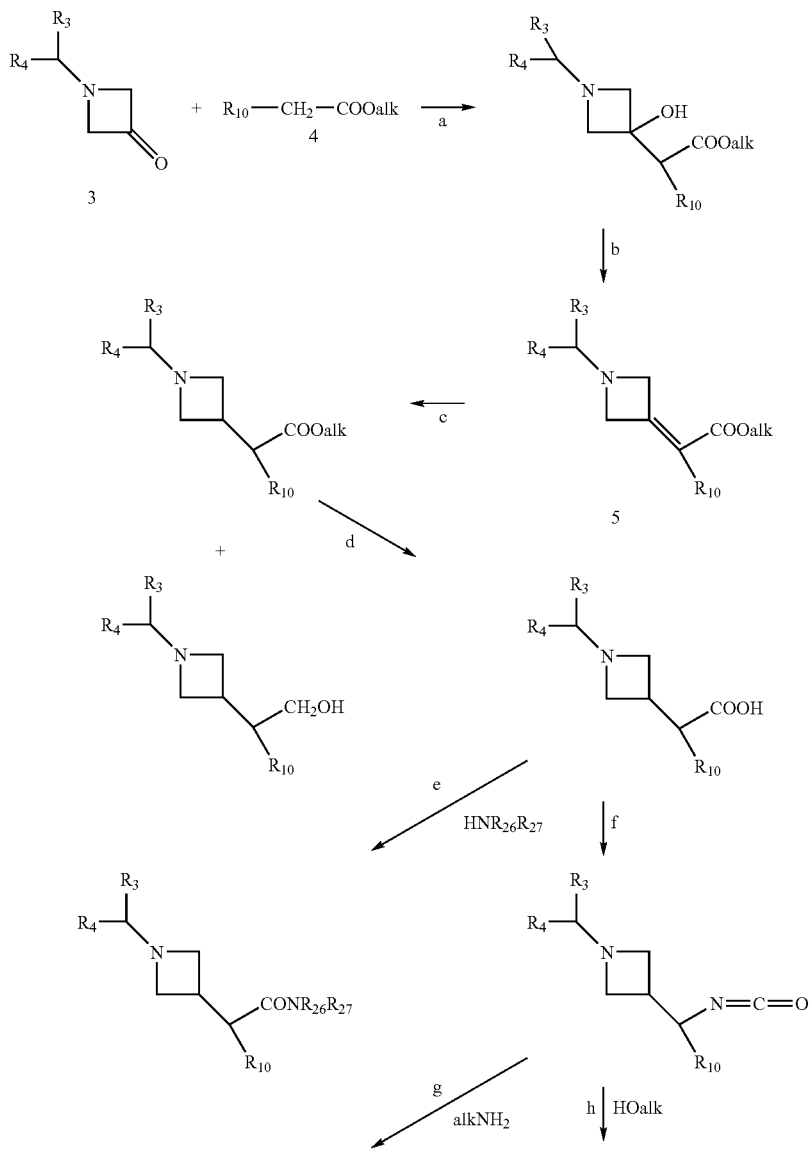

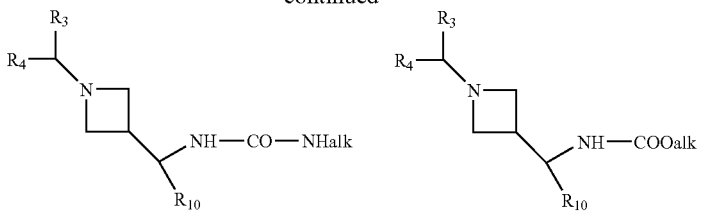

In these formulae, $R_3$, $R_4$, $R_{10}$, $R_{26}$ and $R_{27}$ have the same meanings as in the formula (I) and alk represents an alkyl radical.

The derivatives of formula 4 are commercially available or can be obtained by esterification of the corresponding acids optionally in an activated form, such as the acid chloride. The acids are commercially available or can be obtained from the corresponding methyl derivatives according to the method described by J. P. Hansen et al., J. Heterocycl., 10, 711 (1973).

The reaction a is generally carried out in an inert solvent, such as an ether (for example tetrahydrofuran), in the presence of a strong base, such a tert-butyllithium, n-butyllithium, lithium diisopropylamide or potassium tert-butoxide, at a temperature of between −70° C. and −15° C.

The reaction b is generally carried out by any dehydration method known to a person skilled in the art which makes it possible to dehydrate an alcohol to produce the corresponding alkene and in particular the methods described above.

The reduction c is generally carried out in an inert solvent, such as a (1-4C) aliphatic alcohol, such as methanol, a chlorinated solvent, such as a chloroform or dichloromethane, or a mixture of these solvents, in the presence of $NaBH_4$ at a temperature of between 0° C. and the boiling temperature of the reaction medium.

The reaction d is carried out by any method known to a person skilled in the art which makes it possible to convert an ester to the corresponding acid without effecting the remainder of the molecule. The reaction is preferably carried out in an inert solvent, such as dioxane, in the presence of hydrochloric acid at the boiling temperature of the reaction medium.

The reaction e is carried out by any method known to a person skilled in the art which makes it possible to convert an acid or a reactive derivative of this acid to a carboxamide without affecting the remainder of the molecule. Preferably, when the acid is employed, the reaction is carried out in the presence of a coupling agent used in peptide chemistry, such as a carbodiimide (for example N,N'-dicyclohexylcarbodiimide) or N,N'-carbonyldiimidazole, in an inert solvent, such as an ether (for example tetrahydrofuran or dioxane), an amide (dimethylformamide) or a chlorinated solvent (for example methylene chloride, 1,2-dichloroethane or chloroform), at a temperature of between 0° C. and the reflux temperature of the reaction mixture. When a reactive derivative of the acid is employed, it is possible to react the anhydride, a mixed anhydride or an ester (which can be chosen from activated or nonactivated esters of the acid); the reaction is then carried out either in an organic medium, optionally in the presence of an acid acceptor, such as a nitrogenous organic base (for example trialkylamine, pyridine, 1,8-diazabicyclo[5.4.0]undec-7-ene or 1,5-diazabicyclo[4.3.0]non-5-ene), in a solvent such as is mentioned above or a mixture of these solvents, at a temperature of between 0° C. and the reflux temperature of the reaction mixture, or in a two-phase aqueous/organic medium in the presence of an alkali metal or alkaline earth metal base (sodium hydroxide, potassium hydroxide) or of an alkali metal carbonate or bicarbonate or alkaline earth metal carbonate or bicarbonate at a temperature between 0 and 40° C.

The reaction f is carried out by the Curtius rearrangement in the presence of diphenylphosphoryl azide and the triethylamine in toluene at a temperature in the region of 50° C.

For the reactions g and h, the reaction is carried out directly in the reaction medium of stage g at a temperature in the region of 20° C.

The compounds of formula (I) for which R represents the $CR_1R_2$ radical in which $R_1$ is a hydrogen atom and $R_2$ represents a $—C(R_8)(R_9)(R_{10})$ radical for which $R_8$ is a hydrogen atom, $R_9$ is an $—CH_2—NHR_{28}$ radical and $R_{10}$ represents an $Ar_1$ or $Het_1$ radical can be prepared according to the following reaction scheme:

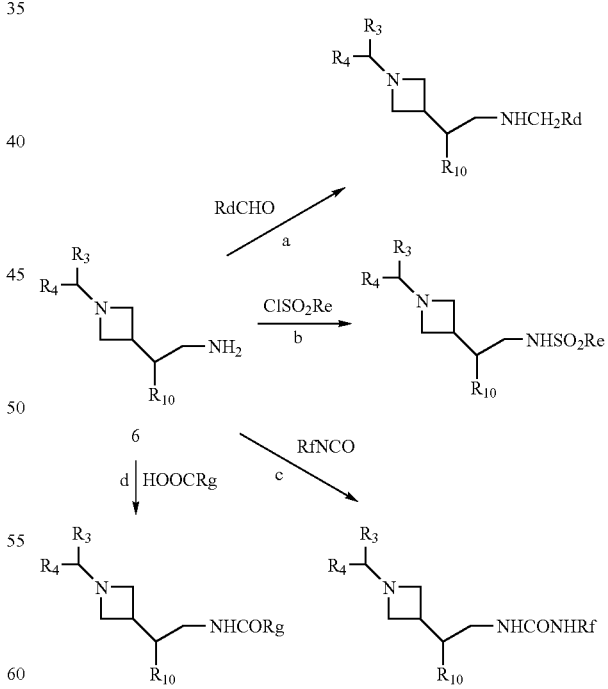

In these formulae, $R_3$, $R_4$ and $R_{10}$ have the same meanings as in the formula (I), Rd represents an alkyl or phenyl radical, Re represents an alkyl radical, Rf represents an alkyl radical, Rg represents an alkyl, cycloalkylalkyl, cycloalkyl or $—(CH_2)_nOH$ radical and n is equal to 1, 2 or 3.

The stage a is generally carried out in an inert solvent, such as a (1-4C) aliphatic alcohol (for example methanol), a chlorinated solvent (for example dichloromethane or dichloroethane) or tetrahydrofuran, in the presence of a base, such as NaBH(OCOCH$_3$)$_3$, at a temperature in the region of 20° C.

The stage b is generally carried out in an inert solvent, such as a halogenated solvent (for example dichloromethane), in the presence of an organic base, such as triethylamine or dimethylaminopyridine, at a temperature of between 0° C. and the boiling temperature of the reaction medium.

The stage c is generally carried out in an inert solvent, such as tetrahydrofuran, dimethylformamide, a chlorinated solvent (for example chloroform or 1,2-dichloroethane) or an aromatic solvent (for example benzene or toluene), at a temperature of between 10° C. and the boiling temperature of the reaction medium.

The stage d is carried out by any method known to a person skilled in the art which makes it possible to convert an acid or a reactive derivative of this acid to a carboxamide without affecting the remainder of the molecule and in particular the preferred methods described above.

The derivative 6 can be obtained according to the following reaction scheme:

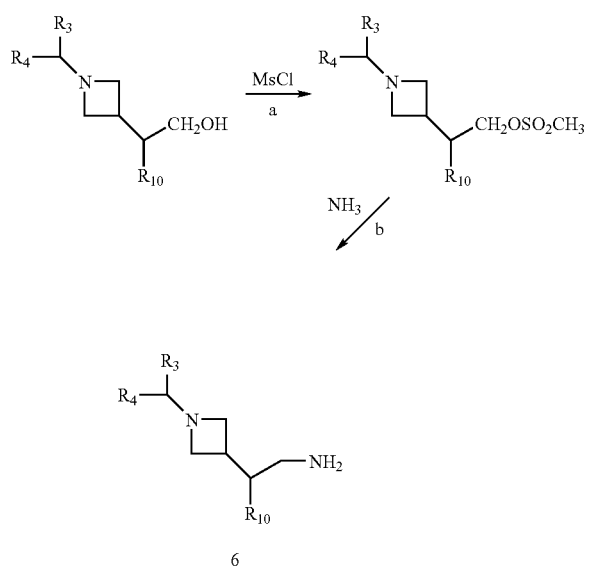

In these formulae, R$_3$, R$_4$ and R$_{10}$ have the same meanings as in the formula (I) and Ms is a methylsulfonyloxy radical.

The stage a is generally carried out in an inert solvent, such as tetrahydrofuran, in the presence of triethylamine at a temperature of between 10 and 20° C.

The stage b is generally carried out with liquid ammonia in methanol, in an autoclave, at a temperature in the region of 60° C.

The compounds of formula (I) in which R represents a CR$_1$R$_2$ radical in which R$_1$ is a hydrogen atom and R$_2$ is a —CONR$_{13}$R$_{14}$ radical can be prepared according to the following reaction scheme:

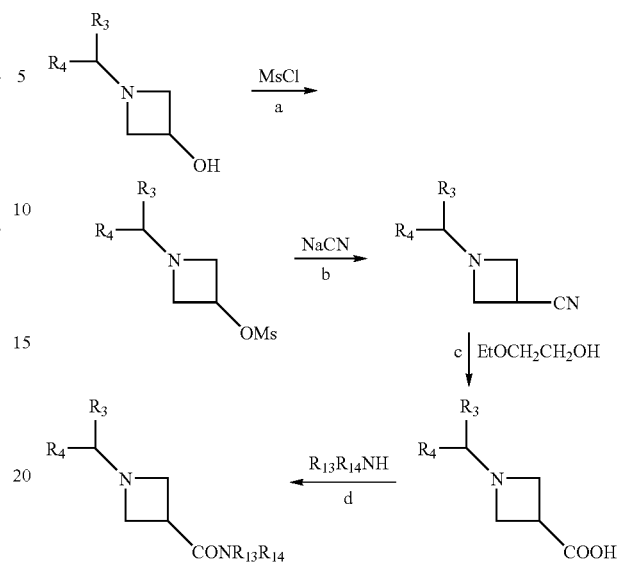

In these formulae, R$_3$, R$_4$, R$_{13}$ and R$_{14}$ have the same meanings as the formula (I), Ms represents a methylsulfonyloxy radical and Et represents ethyl.

The stage a is carried out in the presence of triethylamine in an inert solvent, such as an ether (for example tetrahydrofuran), at a temperature in the region of 0°.

The stage b is generally carried out in an inert solvent, such as a mixture of water and dimethylformamide, at a temperature of between 30 and 75° C.

The stage c is carried out by any method known to a person skilled in the art which makes it possible to convert a cyano compound to the corresponding acid without affecting the remainder of the molecule. The reaction is preferably carried out by means of potassium hydroxide in a (1-4C) aliphatic alcohol (for example ethanol) or in aqueous medium at the boiling temperature of the reaction medium.

The stage d is carried out by any method known to a person skilled in the art which makes it possible to convert an acid or a reactive derivative of this acid to a carboxamide without affecting the remainder of the molecule and in particular the preferred methods described above.

The compounds of formula (I) for which R represents a CR$_1$R$_2$ radical in which R$_1$ is a hydrogen atom and R$_2$ is a —CH$_2$—CONR$_{13}$R$_{14}$ radical can be prepared according to the following reaction scheme:

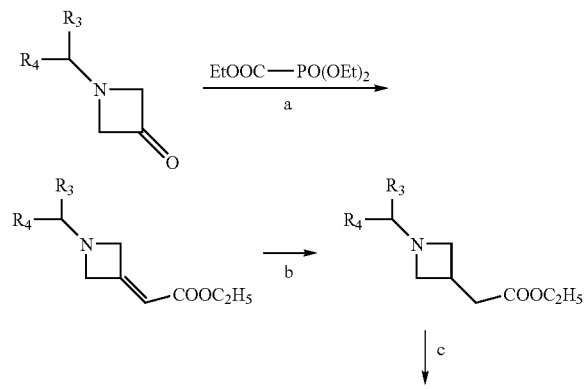

-continued

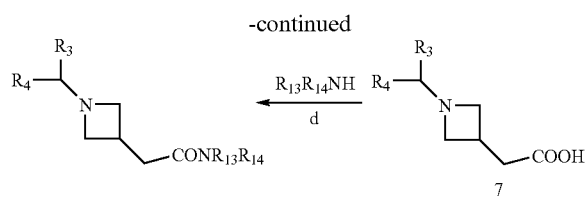

In these formulae, $R_3$, $R_4$, $R_{13}$ and $R_{14}$ have the same meanings as in the formula (I) and Et represents an ethyl radical.

The reaction a is generally carried out in an inert solvent, such as tetrahydrofuran, in the presence of a base, such as sodium hydride or an alkali metal carbonate (for example potassium carbonate), at a temperature between 20° C. and the boiling temperature of the reaction medium.

The reaction b is generally carried out by means of $NaBH_4$ in ethanol at a temperature in the region of 0° C.

The reaction c is carried out by any method known to a person skilled in the art which makes it possible to convert an ester to the corresponding acid without affecting the remainder of the molecule. The reaction is preferably carried out in an inert solvent, such as dioxane, in the presence of hydrochloric acid at the boiling temperature of the reaction medium.

The reaction d is carried out by any method known to a person skilled in the art which makes it possible to convert an acid or a reactive derivative of this acid to a carboxamide without affecting the remainder of the molecule and in particular the preferred methods described above.

The intermediates 7 can also be obtained by malonic synthesis according to the following reaction scheme:

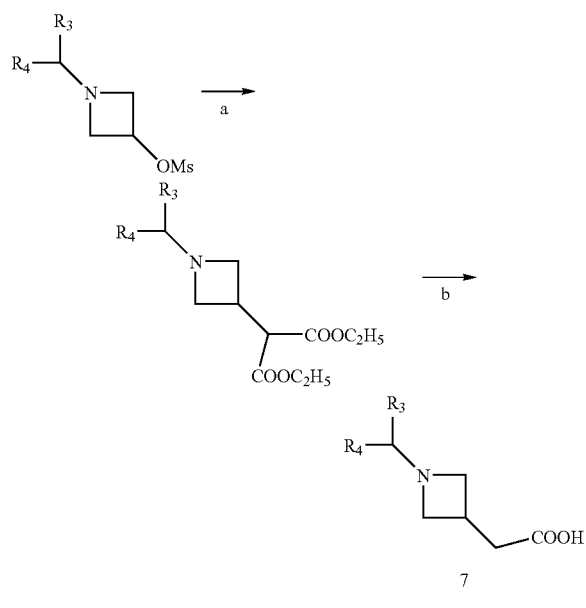

In these formulae, Ms represents a methylsulfonyloxy radical and $R_3$ and $R_4$ have the same meanings as in the formula (I).

The reaction a is generally carried out by reaction with diethyl malonate in an inert solvent, such as tetrahydrofuran, in the presence of freshly prepared sodium ethoxide at the boiling temperature of the reaction medium.

The reaction b is generally carried out in an aqueous hydrochloric acid solution at the boiling temperature of the reaction medium.

The compounds 8 can also be obtained according to the following reaction scheme:

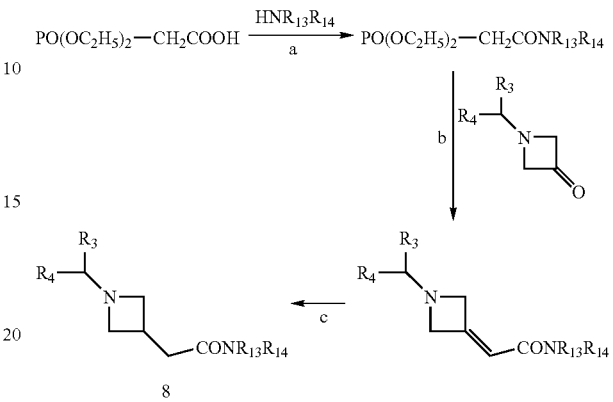

In these formulae, $R_3$, $R_4$, $R_{13}$ and $R_{14}$ have the same meanings as in the formula (I).

Stage a is carried out by any method known to a person skilled in the art which makes it possible to convert an acid or a reactive derivative of this acid to a carboxamide without affecting the remainder of the molecule and in particular the preferred methods described above.

Stage b is generally carried out in an inert solvent, such as tetrahydrofuran, in the presence of a base, such as sodium hydride or potassium carbonate, at a temperature of between 20° C. and the boiling temperature of the reaction mixture.

The reduction of stage c is generally carried out by means of $NaBH_4$ in ethanol at a temperature in the region of 20° C.

The compounds of formula (I) for which R represents a $CR_1R_2$ radical in which $R_1$ is a hydrogen atom and $R_2$ represents an $-SOR_6$ or $-SO_2R_6$ radical can be prepared according to the following reaction scheme:

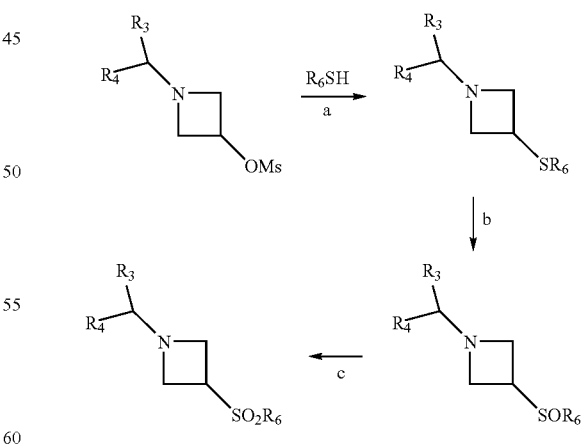

In these formulae, $R_3$, $R_4$ and $R_6$ have the same meanings as in the formula (I) and Ms is a methylsulfonyloxy radical.

Stage a is generally carried out in an inert solvent, such as tetrahydrofuran, in the presence of an inorganic base, such as sodium hydride, at a temperature of between 0° C. and the boiling temperature of the reaction medium.

Stage b is generally carried out by any method known to a person skilled in the art for the oxidation of a sulfur derivative, such as those described by M. Hudlicky, Oxidations in Organic Chemistry, ACS Monograph, 186, 252–263 (1990). For example, the reaction is carried out by the action of an organic peroxyacid or a salt of such an peroxyacid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or inorganic peracids or a salt of such an acid (for example periodic or persulfuric acid) in an inert solvent, such as a chlorinated solvent (for example chloroform or dichloromethane), at a temperature of between 0 and 25° C. or else by means of oxone in a water/alcohol (methanol, ethanol) mixture.

Stage c is generally carried out by any method known to a person skilled in the art for the oxidation of a sulfinyl derivative. Preferably, the reaction is carried out by the action of an organic peroxyacid or a salt of such a peroxyacid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or else by means of oxone in a water/alcohol (methanol, ethanol) mixture.

The compounds of formula (I) for which R represents a $CR_1R_2$ radical in which $R_1$ is a hydrogen atom and $R_2$ represents a —$COR_6$ or —CO-cycloalkyl radical can be prepared according to the following reaction scheme:

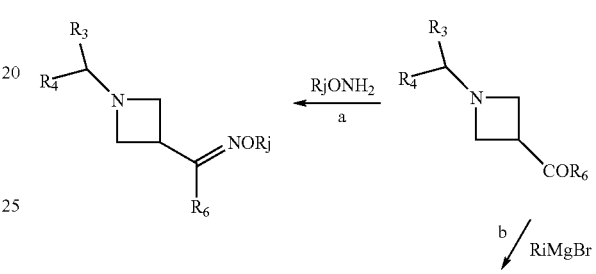

In these formulae, $R_3$ and $R_4$ have the same meanings as in the formula (I) and Rh has the same meanings as $R_6$ or represents a cycloalkyl radical (3 to carbon atoms).

Stage a is carried out by any method known to a person skilled in the art which makes it possible to convert an acid or a reactive derivative of this acid to a carboxamide without affecting the remainder of the molecule and in particular the preferred methods described above.

Stage b is generally carried out in an inert solvent, such as an ether, for example tetrahydrofuran, at a temperature in the region of 0° C. The organomagnesium compounds are prepared according to methods known to a person skilled in the art, such as those described in the examples.

The compounds of formula (I) for which $R_1$ is a hydrogen atom and $R_2$ is a —$C(OH)(R_6)(R_{12})$, —$C(OH)(R_6)$(alkyl), —C(=NO—$CH_2$—CH=$CH_2$)$R_6$ or —C(=NOalk)$R_6$ radical can be prepared according to the following reaction scheme:

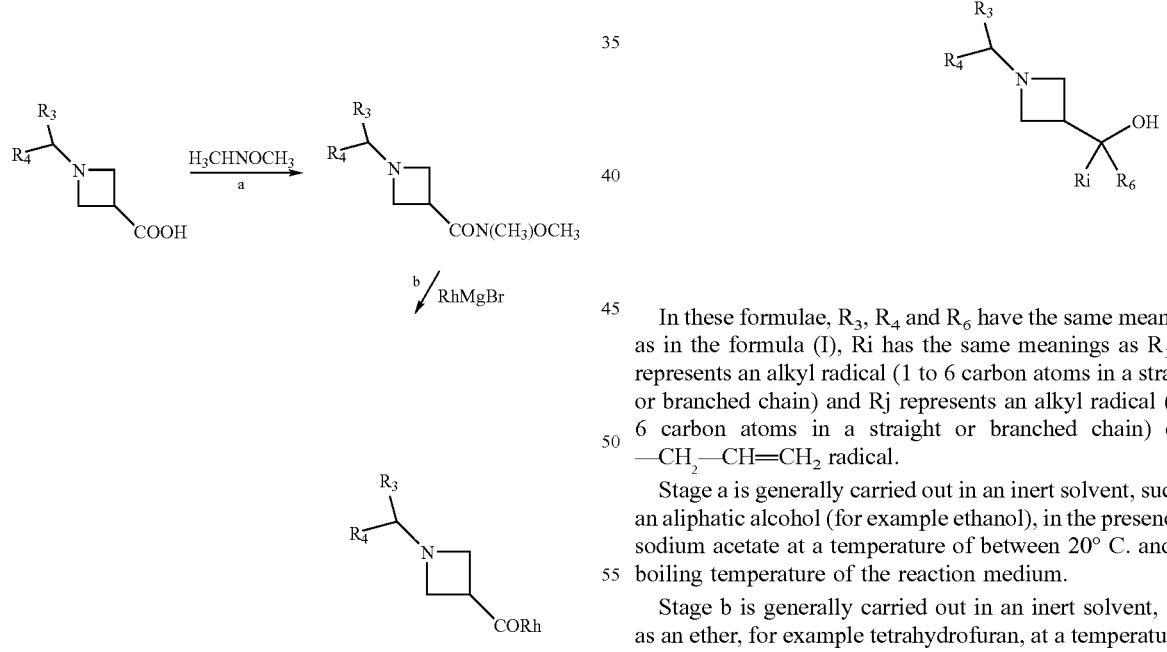

In these formulae, $R_3$, $R_4$ and $R_6$ have the same meanings as in the formula (I), Ri has the same meanings as $R_{12}$ or represents an alkyl radical (1 to 6 carbon atoms in a straight or branched chain) and Rj represents an alkyl radical (1 to 6 carbon atoms in a straight or branched chain) or a —$CH_2$—CH=$CH_2$ radical.

Stage a is generally carried out in an inert solvent, such as an aliphatic alcohol (for example ethanol), in the presence of sodium acetate at a temperature of between 20° C. and the boiling temperature of the reaction medium.

Stage b is generally carried out in an inert solvent, such as an ether, for example tetrahydrofuran, at a temperature in the region of 0° C. The organomagnesium compounds are prepared according to methods known to a person skilled in the art, such as those described in the examples.

The compounds of formula (I) for which R represents a $CR_1R_2$ radical in which $R_1$ is a hydrogen atom and $R_2$ represents a —$CH(R_6)NR_{31}R_{32}$, in which $R_{31}$ and $R_{32}$ are hydrogen atoms, —$CH(R_6)NHSO_2$alk, —$CH(R_6)$NHCONHalk or —$CH(R_6)NHCOR_{31}$ radical can be prepared according to the following reaction scheme:

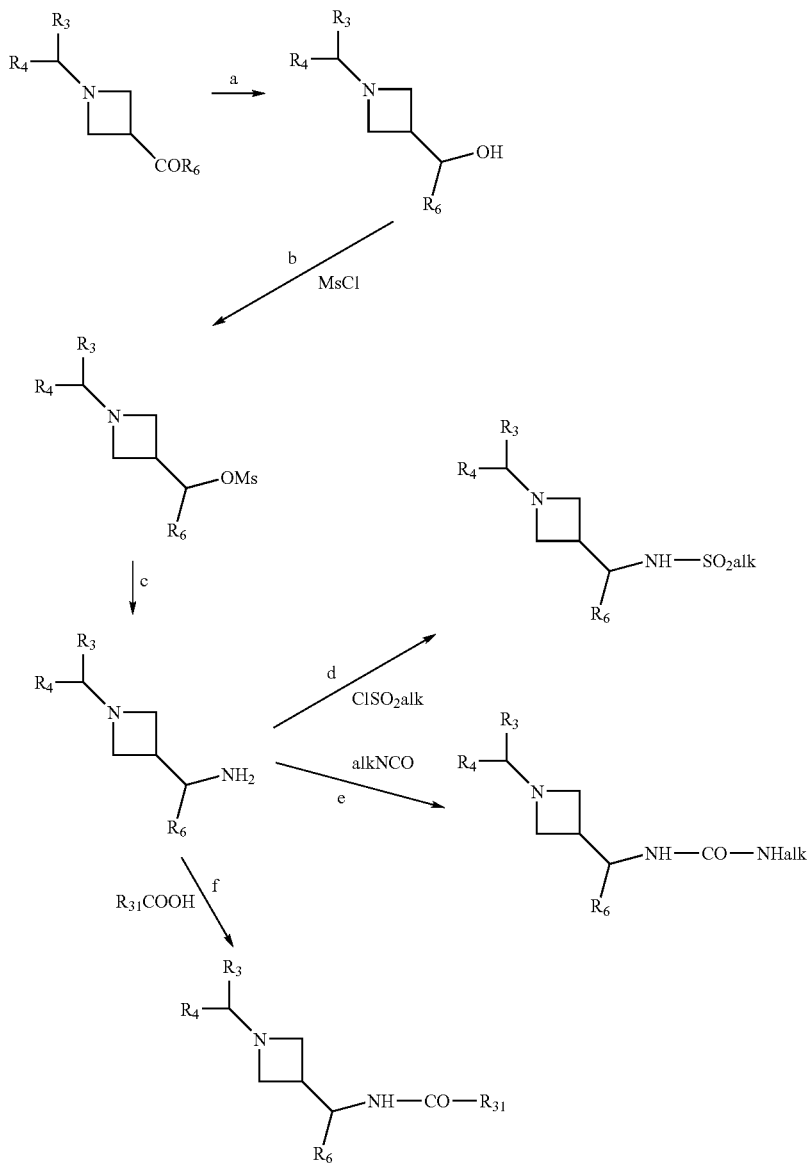

In these formulae, $R_3$, $R_4$, $R_6$ and $R_{31}$ have the same meanings as in the formula (I), Ms represents a methylsulfonyloxy radical and alk represents an alkyl radical.

The reaction a is generally carried out by means of $NaBH_4$ in ethanol at a temperature in the region of 20° C.

Stage b is carried out in the presence of triethylamine in an inert solvent, such as an ether (for example tetrahydrofuran), at a temperature in the region of 0° C.

Stage c is carried out by means of liquid ammonia in methanol, in an autoclave, at a temperature in the region of 60°.

Stage d is generally carried out in an inert solvent, such as a halogenated solvent (for example dichloromethane) or tetrahydrofuran, in the presence of an organic base, such as triethylamine or dimethylaminopyridine, at a temperature in the region of 20° C.

Stage e is carried out by any method known to a person skilled in the art which makes it possible to convert an acid or a reactive derivative of this acid to a carboxamide without affecting the remainder of the molecule and in particular the preferred methods described above.

Stage f is generally carried out in an inert solvent, such as tetrahydrofuran, dimethylformamide, a chlorinated solvent (for example chloroform or dichloroethane) or an aromatic solvent (for example benzene or toluene), at a temperature of between 10° C. and the boiling temperature of the reaction medium.

The compounds of formula (I) for which R represents a $CR_1R_2$ radical in which $R_1$ is a hydrogen atom and $R_2$ represents a —$CH(R_6)NR_{31}R_{32}$ radical, $R_{31}$ is a hydrogen atom and $R_{32}$ is an alkyl, $Ar_1$ or -alk-$Ar_1$ radical can be prepared by reaction of a halide $HalR_{31}$ with a compound of formula (I) for which R represents a $CR_1R_2$ radical in which $R_1$ is a hydrogen atom and $R_2$ represents a —$CH(R_6)NR_{31}R_{32}$ radical and $R_{31}$ and $R_{32}$ are hydrogen atoms.

This reaction is carried out in an inert polar solvent, such as acetonitrile, tetrahydrofuran or dimethylformamide, in the presence of an organic or inorganic base (alkali metal carbonate (for example sodium or potassium carbonate) or trialkylamine (for example triethylamine or dimethylaminopyridine)) at a temperature of between 0° C. and the boiling temperature of the solvent, optionally in the presence of palladium or of one of its salts or complexes.

The compounds of formula (I) for which R represents a $CR_1R_2$ radical in which $R_1$ is a hydrogen atom and $R_2$ represents a —$CH(R_6)NR_{31}R_{32}$ radical, $R_{31}$ is a hydrogen atom and $R_{32}$ is an alkyl radical can also be prepared by reaction of a corresponding compound of formula (I) for which R represents a $CR_1R_2$ radical in which $R_1$ is a hydrogen atom and $R_2$ represents a —CO—$R_6$ radical with an amine $HNR_{31}R_{32}$ for which $R_{31}$ is a hydrogen atom and $R_{32}$ is an alkyl radical.

This reaction is generally carried out in an inert solvent, such as a chlorinated solvent (for example dichloromethane or dichloroethane), in the presence of a reducing agent, such as sodium triacetoxyborohydride, at a temperature of between 0° C. and 70° C.

The compounds of formula (I) for which R represents a $CR_1R_2$ radical in which $R_1$ is a hydrogen atom and $R_2$ represents a —$CH(R_6)NR_{31}R_{32}$ radical and $R_{31}$ and $R_{32}$ are alkyl, $Ar_1$ or -alk-$Ar_1$ radicals can be prepared by reaction of a halide $HalR_{32}$ with a compound of formula (I) for which R represents a $CR_1R_2$ radical in which $R_1$ is a hydrogen atom and $R_2$ represents a —$CH(R_6)NR_{31}R_{32}$ radical, $R_{31}$ is a hydrogen atom and $R_{32}$ is an alkyl, $Ar_1$ or -alk-$Ar_1$ radical.

This reaction is carried out in an inert polar solvent, such as acetonitrile, tetrahydrofuran or dimethylformamide, in the presence of an organic or inorganic base (alkali metal carbonate (for example sodium or potassium carbonate) or trialkylamine (for example triethylamine or dimethylaminopyridine)) at a temperature of between 0° C. and the boiling temperature of the solvent, optionally in the presence of palladium or of one of its salts or complexes.

The compounds of formula (I) for which R represents a $CR_1R_2$ radical in which $R_1$ is a hydrogen atom and $R_2$ represents a —$CH(R_6)NR_{31}R_{32}$ radical, $R_{31}$ is a hydrogen atom and $R_{32}$ is a (2-6C) alkyl or -(2-6C)alkyl-$Ar_1$ radical can be prepared by reaction of an aldehyde RaCHO for which Ra is an alkyl or -alk-$Ar_1$ radical with a compound of formula (I) for which R represents a $CR_1R_2$ radical in which $R_1$ is a hydrogen atom and $R_2$ represents a —$CH(R_6)NR_{31}R_{32}$ radical and $R_{31}$ and $R_{32}$ are hydrogen atoms.

This reaction is carried out in an inert solvent, such as dichloromethane, dichloroethane, toluene or tetrahydrofuran, at a temperature of between 0° C. and 50° C. in the presence of a reducing agent, such as sodium triacetoxyborohydride or sodium cyanoborohydride.

The compounds of formula (I) for which R represents a $CR_1R_2$ radical in which $R_1$ is a hydrogen atom and $R_2$ represents a —$CH(R_6)NR_{31}R_{32}$ radical, $R_{31}$ is an alkyl, $Ar_1$ or -alk-$Ar_1$ radical and $R_{32}$ is a (2-6C) alkyl or -(2-6C)alkyl-$Ar_1$ radical can be prepared by reaction of an aldehyde RaCHO for which Ra is an alkyl or alk-$Ar_1$ radical with a compound of formula (I) for which R represents a $CR_1R_2$ radical in which $R_1$ is a hydrogen atom and $R_2$ represents a —$CH(R_6)NR_{31}R_{32}$ radical, $R_{31}$ is a hydrogen atom and $R_{32}$ is an alkyl, $Ar_1$ or -alk-$Ar_1$ radical.

This reaction is carried out in an inert solvent, such as dichloromethane, dichloroethane, toluene or tetrahydrofuran, at a temperature of between 0° C. and 50° C. in the presence of a reducing agent, such as sodium triacetoxyborohydride or sodium cyanoborohydride.

The compounds of formula (I) for which R represents a $CR_1R_2$ radical in which $R_1$ is a hydrogen atom and $R_2$ represents a —$CH(R_6)NR_{31}R_{32}$ radical and $R_{31}$ and $R_{32}$ form, with the nitrogen atom to which they are attached, a heterocycle chosen from aziridinyl, azetidinyl, pyrrolidinyl or piperidinyl, can be prepared by reaction of a dihalide, Hal-(2-5C)alk-Hal, with a compound of formula (I) for which R represents a $CR_1R_2$ radical in which $R_1$ is a hydrogen atom and $R_2$ represents a —$CH(R_6)NR_{31}R_{32}$ radical and $R_{31}$ and $R_{32}$ are hydrogen atoms.

This reaction is carried out in an inert polar solvent, such as acetonitrile, tetrahydrofuran or dimethylformamide, in the presence of an organic or inorganic base (alkali metal carbonate (for example sodium or potassium carbonate) or trialkylamine (for example triethylamine or dimethylaminopyridine)) at a temperature of between 0° C. and the boiling temperature of the solvent, optionally in the presence of palladium or of one of its salts or complexes.

The compounds of formula (I) for which R represents a $CR_1R_2$ radical in which $R_1$ is a hydrogen atom and $R_2$ represents a —$CH_2$—$COR_6$, —$CH_2$—$CH(R_6)NR_{31}R_{32}$ or —$CH_2$—$C(=NOalk)R_6$ radical can be prepared according to the following reaction scheme:

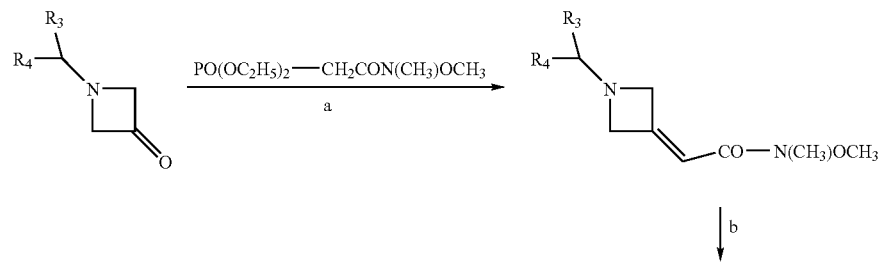

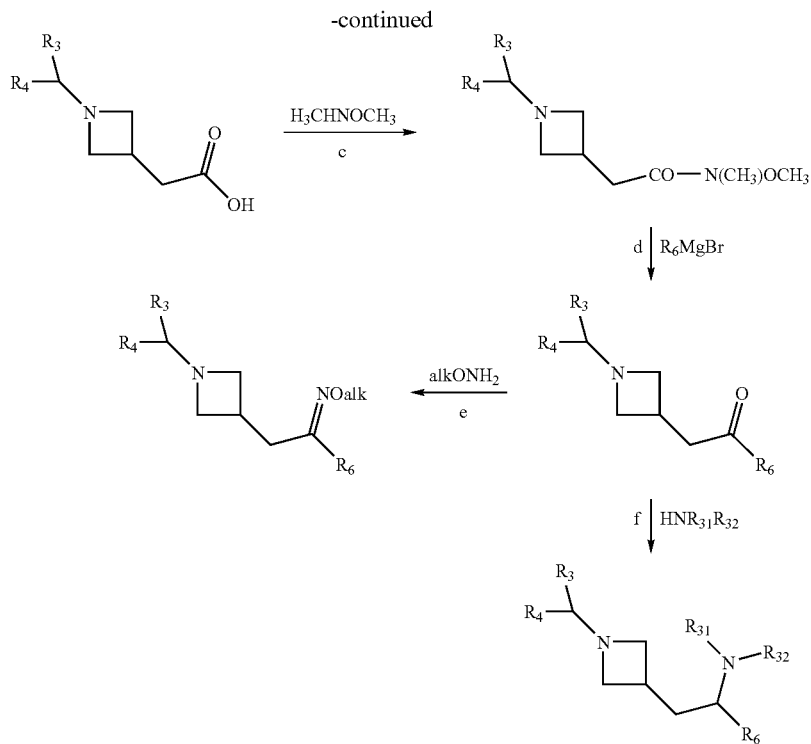

-continued

In these formulae, $R_3$, $R_4$, $R_6$, $R_{31}$ and $R_{32}$ have the same meaning as in the formula (I) and alk represents an alkyl radical.

Stage a is generally carried out in a solvent, such as tetrahydrofuran, at a temperature of between 20° C. and the boiling temperature of the reaction medium.

Stage b is generally carried out in an inert solvent, such as an aliphatic alcohol (for example methanol), a chlorinated solvent (chloroform, dichloromethane) or a mixture of these solvents, in the presence of a reducing agent, such as $NaBH_4$, at a temperature of between 0° C. and the boiling temperature of the reaction medium.

Stage c is carried out by any method known to a person skilled in the art which makes it possible to convert an acid or a reactive derivative of this acid to a carboxamide without affecting the remainder of the molecule and in particular the preferred methods described above.

Stage d is generally carried out in an inert solvent, such as an ether, for example tetrahydrofuran, at a temperature in the region of 0° C. The organomagnesium compounds are prepared according to methods known to a person skilled in the art, such as those described in the examples.

Stage e is generally carried out in an inert solvent, such as a 1-4C. aliphatic alcohol, for example methanol, in the presence of sodium acetate at a temperature of between 20° C. and the boiling temperature of the reaction medium.

Stage f is carried out in an inert solvent, such as a chlorinated solvent (for example dichloromethane or dichloroethane), in the presence of a reducing agent, such as sodium triacetoxyborohydride, at a temperature of between 0° C. and 70° C.

The compounds of formula (I) for which R represents a $CR_1R_2$ radical in which $R_1$ represents a cyano, —S-alk-$NR_{16}R_{17}$, alkyl or —$NR_{20}R_{21}$ radical and $R_2$ represents a —$C(R_8)$ $(R_{11})$ $(R_{12})$ radical in which $R_8$ is a hydrogen atom can be prepared according to the following reaction scheme:

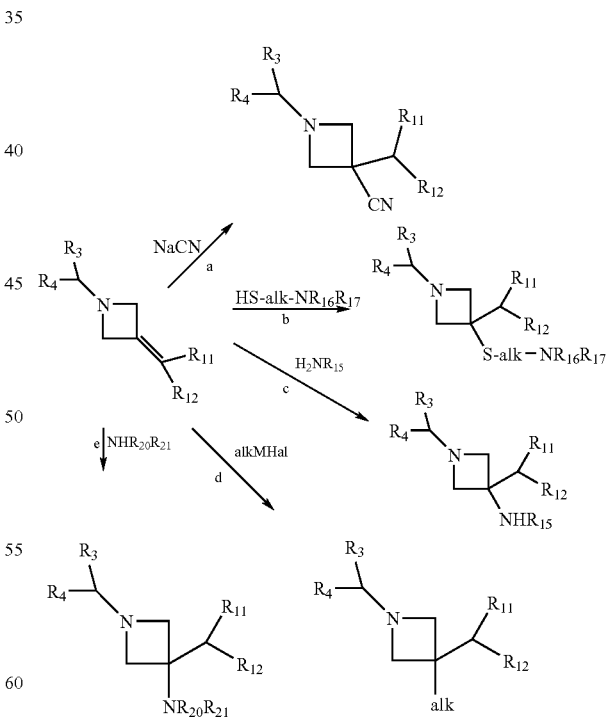

In these formulae, $R_3$, $R_4$, $R_{11}$, $R_{12}$, $R_{15}$, $R_{16}$ and $R_{17}$ have the same meanings as in the formula (I), alk represents an alkyl radical, Hal represents a halogen atom and M represents a metal and preferably copper.

Stage a is preferably carried out in a polar solvent, such as dimethyl sulfoxide, at a temperature of between 20 to 50° C.

Stage b is preferably carried out in an inert solvent, such as dimethyl sulfoxide, tetrahydrofuran or acetonitrile, in the presence of a base, such as an alkali metal carbonate (for example potassium carbonate) or ammonium hydroxide, at a temperature of between 20° C. and the boiling temperature of the reaction medium.

Stage c is preferably carried out in an inert solvent, such as dimethyl sulfoxide, tetrahydrofuran or acetonitrile, in the presence of a base, such as an alkali metal carbonate (for example potassium carbonate) or ammonium hydroxide, at a temperature of between 20° C. and the boiling point of the reaction medium.

Stage d is preferably carried out in an inert solvent, such as an ether (ethyl ether) or tetrahydrofuran, at a temperature of between −78° C. and 20° C.

Stage e is preferably carried out in an inert solvent, such as dimethyl sulfoxide, tetrahydrofuran, acetonitrile, dichloromethane or dichloroethane, in the presence of a base, such as an alkali metal carbonate (for example potassium carbonate) or ammonium hydroxide, at a temperature of between 20° C. and the boiling temperature of the reaction medium.

The compounds of formula (I) for which R represents a $CR_1R_2$ radical in which $R_1$ represents a —$NR_{18}R_{19}$ radical and $R_{18}$ and $R_{19}$ represent a hydrogen atom can be prepared by reduction of a corresponding compound of formula (I) for which R represents a $CR_1R_2$ radical in which $R_1$ represents a cyano radical.

This reaction is generally carried out in an inert solvent, such as tetrahydrofuran, ethyl ether or toluene, at a temperature of between 0° C. and the boiling temperature of the reaction medium, in the presence of a reducing agent, such as aluminum hydride.

The compounds of formula (I) for which R represents a $CR_1R_2$ radical in which $R_1$ represents an -alk-$NR_{18}R_{19}$ radical, $R_{18}$ represents the hydrogen atom and $R_{19}$ represents an alkyl, cycloalkyl, cycloalkylalkyl, cycloalkylcarbonyl, —$SO_2$alk, —CO—NHalk or —COOalk radical can be prepared by reaction of a halide Hal$R_{19}$, Hal represents a halogen, with a compound of formula (I) for which R represents a $CR_1R_2$ radical in which $R_1$ represents an -alk-$NR_{18}R_{19}$ radical and $R_{18}$ and $R_{19}$ represent a hydrogen atom.

This reaction is carried out in an inert polar solvent, such as acetonitrile, tetrahydrofuran or dimethylformamide, in the presence of an organic or inorganic base (alkali metal carbonate (for example sodium or potassium carbonate) or trialkylamine (for example triethylamine or dimethylaminopyridine)) at a temperature of between 0° C. and the boiling temperature of the solvent, optionally in the presence of palladium or of one of its salts or complexes.

The compounds of formula (I) for which R represents a $CR_1R_2$ radical in which $R_1$ represents an -alk-$NR_{18}R_{19}$ radical, $R_{18}$ represents an alkyl radical and $R_{19}$ represents an alkyl, cycloalkyl, cycloalkylalkyl, cycloalkylcarbonyl, —$SO_2$alk, —CO—NHalk or —COOalk radical can be prepared by reaction of an alkyl halide with a compound of formula (I) for which R represents a $CR_1R_2$ radical in which $R_1$ represents an -alk-$NR_{18}R_{19}$ radical, $R_{18}$ represents a hydrogen atom and $R_{19}$ represents an alkyl, cycloalkyl, cycloalkylalkyl, cycloalkylcarbonyl, —$SO_2$alk, —CO—NHalk or —COOalk radical.

This reaction is carried out in an inert polar solvent, such as acetonitrile, tetrahydrofuran or dimethylformamide, in the presence of an organic or inorganic base (alkali metal carbonate (for example sodium potassium carbonate) or trialkylamine (for example triethylamine or dimethylaminopyridine)) at a temperature of between 0° C. and the boiling temperature of the solvent, optionally in the presence of palladium or of one of its salts or complexes.

The compounds of formula (I) for which R represents a $CR_1R_2$ radical in which either $R_1$ represents a hydrogen atom and $R_2$ represents a —$C(R_8)(R_9)(R_{10})$ or —$C(R_8)(R_{11})(R_2)$ radical or $R_1$ represents an alkyl, NH—$R_{15}$, cyano, —S-alk-$NR_{16}R_{17}$, -alk-$NR_{18}R_{19}$ or —$NR_{20}R_{21}$ radical and $R_2$ represents a —$C(R_8)(R_{11})(R_{12})$ radical and $R_8$ represents an alkyl radical can be prepared by alkylation of a corresponding compound of formula (I) for which $R_8$ is a hydrogen atom.

This reaction is preferably carried out by means of a base, such as an alkali metal hydride (for example sodium hydride), an alkali metal amide (for example sodium amide) or an organometallic derivative, in an inert solvent, such as an aliphatic ether (ethyl ether) or tetrahydrofuran, at a temperature of between −78° C. and 30° C. by means of an alkylating agent, such as an alkyl halide or an alkyl sulfonate.

The compounds of formula (I) for which R represents a $C=C(R_7)SO_2$alk radical can also be prepared according to the following reaction scheme:

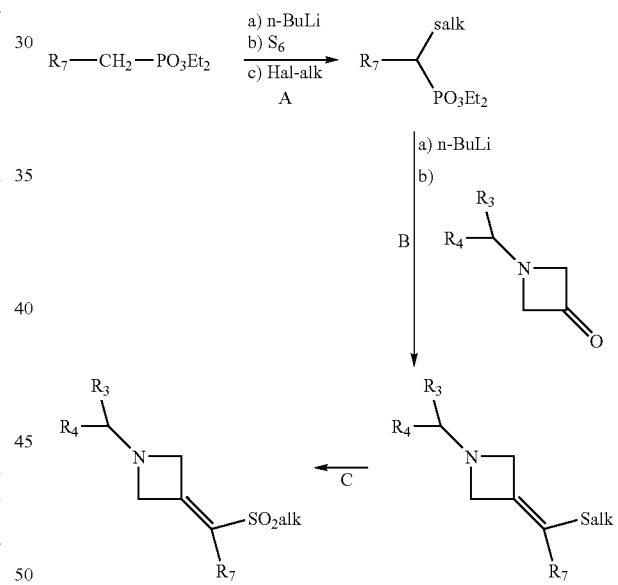

In these formulae, $R_3$, $R_4$ and $R_7$ have the same meanings as in the formula (I), alk represent an alkyl radical and Hal represents a halogen atom.

The reaction A is generally carried out in an inert solvent, such as an ether (for example ethyl ether), in the presence of a strong base, such as tert-butyllithium or n-butyllithium, at a temperature of between −70° C. and −50° C., followed by addition of sulfur and then of an alkyl halide (for example iodide or bromide).

The reaction B is generally carried out in an inert solvent, such as an ether (for example tetrahydrofuran), in the presence of a strong base, such as tert-butyllithium or n-butyllithium, at a temperature of between −70° C. and −50° C., followed by addition of the azetidin-3-one, return to ambient temperature and hydrolysis.

The reaction C is carried out by any known method which makes it possible to oxidize a sulfur derivative without affecting the remainder of the molecule, such as those described above.

The compounds of formula (I) for which R represents a $CHR_{33}$ radical and $R_{33}$ represents an —$NHCOR_{34}$ radical can be prepared according to the following reaction scheme:

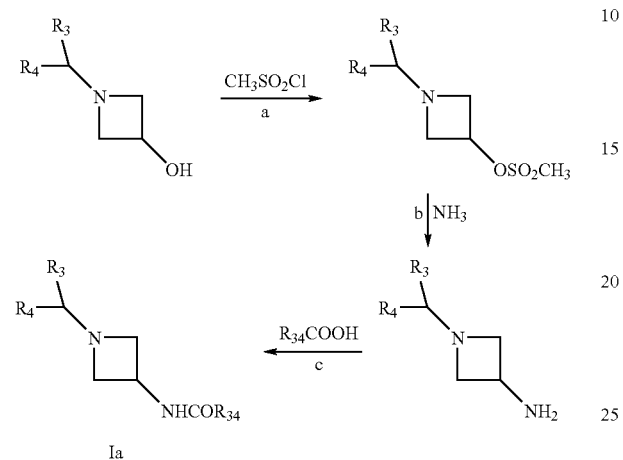

Ia

In these formulae, $R_3$, $R_4$ and $R_{34}$ have the same meanings as in the formula (I).

Stage a is generally carried out in an inert solvent, such as tetrahydrofuran, dioxane or a chlorinated solvent (for example dichloromethane or chloroform), at a temperature of between 15° C. and 30° C. in the presence of a base, such as a trialkylamine (for example triethylamine or dipropylethylamine), or in pyridine at a temperature of between 0° C. and 30° C.

Stage b is preferably carried out in methanol, in an autoclave, at a temperature of between 50 and 70° C.

Stage c is generally carried out in the presence of a coupling agent used in peptide chemistry, such as a carbodiimide (for example 1-(3-dimethylaminopropyl)-3-ethylcarbodiimide or N,N'-dicyclohexylcarbodiimide) or N,N'-carbonyldiimidazole, in an inert solvent, such as an ether (for example tetrahydrofuran or dioxane), an amide (dimethylformamide) or a chlorinated solvent (for example methylene chloride, 1,2-dichloroethane or chloroform), at a temperature of between 0° C. and the boiling temperature of the reaction mixture. Use may also be made of a reactive derivative of the acid, such as an acid chloride, optionally in the presence of an acid acceptor, such as a nitrogenous organic base (for example trialkylamine, pyridine, 1,8-diazabicyclo-[5.4.0]undec-7-ene or 1,5-diazabicyclo[4.3.0]non-5-ene), in a solvent such as mentioned above, or a mixture of these solvents, at a temperature of between 0° C. and the boiling temperature of the reaction mixture.

The $R_{34}COOH$ derivatives are commercially available or can be obtained according to the methods described in R. C. Larock, Comprehensive Organic Transformations, VCH editor.

The compounds of formula (I) for which R represents a $CHR_{33}$ radical and $R_{33}$ represents an —$N(R_{35})$—Y—$R_{36}$ radical can be prepared according to the following reaction scheme:

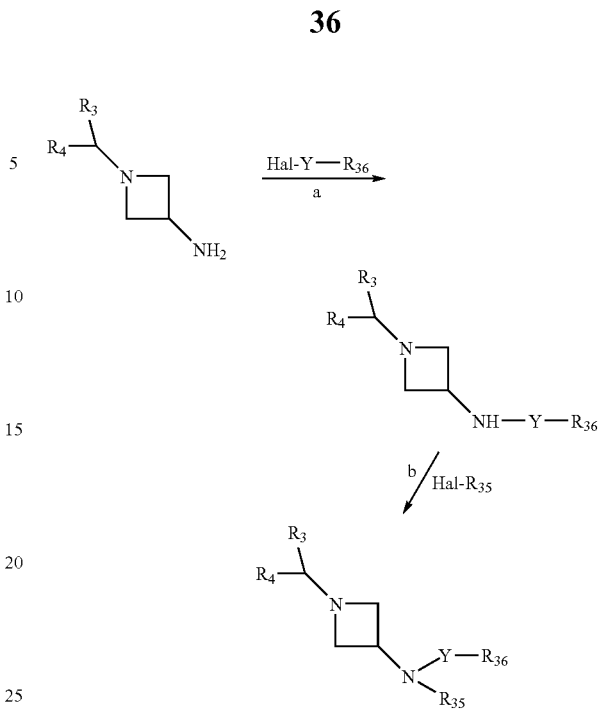

In these formulae, Y, $R_4$, $R_3$ and $R_{36}R_{35}$ have the same meanings as in the formula (I) and Hal represents a halogen atom and preferably an iodine, chlorine or bromine atom.

Stage a is generally carried out in an inert solvent, such as tetrahydrofuran, dioxane or a chlorinated solvent (for example dichloromethane or chloroform), in the presence of an amine, such as a trialkylamine (for example triethylamine), at a temperature of between 5° C. and 20° C.

Stage b is generally carried out in an inert solvent, such as tetrahydrofuran, in the presence of sodium hydride at a temperature 0° C. and the boiling temperature of the reaction medium.

The Hal-$SO_2R_{36}$ derivatives are commercially available or can be obtained by halogenation of the corresponding sulfonic acids, in particular in situ in the presence of chlorosulfonyl isocyanate and of alcohol, in an halogenated solvent (for example dichloromethane or chloroform).

The Hal-CO—$R_{36}$ derivatives are commercially available or can be prepared according to the methods described in R. C. Larock, Comprehensive Organic Transformations, VCH editor.

The compounds of formula (I) can also be prepared according to the following reaction scheme:

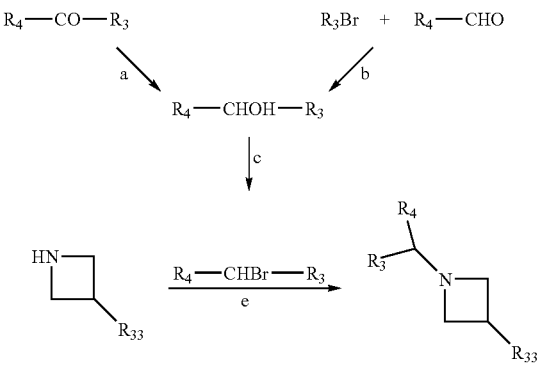

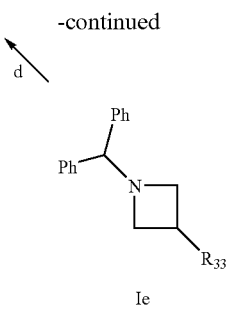

Ie

In these formulae, $R_{34}$, $R_4$ and $R_3$ have the same meanings as in the formula (I) and Ph represents a phenyl.

Stage a is generally carried out in an alcohol, such as methanol, in the presence of sodium borohydride at a temperature in the region of 20° C.

In stage b, the magnesium product from the bromine derivative is prepared and is reacted in an inert solvent, such as ethyl ether or tetrahydrofuran, at a temperature of between 0° C. and the boiling temperature of the reaction medium.

Stage c is carried out by means of a halogenating agent, such as hydrobromic acid, thionyl bromide, thionyl chloride or a mixture of triphenylphosphine and of carbon tetrabromide or tetrachloride, in acetic acid or an inert solvent, such as dichloromethane, chloroform, carbon tetrachloride or toluene, at a temperature of between 0° C. and the boiling temperature of the reaction medium.

Stage d is carried out by means of hydrogen in the presence of palladium-charcoal in an alcohol, such as methanol, at a temperature in the region of 20° C.

Stage e is carried out in an inert solvent, such as acetonitrile, in the presence of an alkali metal carbonate (for example potassium carbonate) and of potassium iodide at a temperature of between 20° C. and the boiling temperature of the reaction medium.

The $R_3Br$ derivatives and the $R_4$—CHO derivatives are commercially available or can be obtained according to the methods described, for example, by R. C. Larock, Comprehensive Organic Transformations, VCH editor.

The compounds of formula (I) for which R represents a $CHR_{33}$ radical and $R_{33}$ represents an —N($R_{35}$)—Y—$R_{36}$ radical in which $R_{36}$ is a phenyl radical substituted by hydroxyl can also be prepared by hydrolysis of a corresponding compound of formula (I) for which $R_{33}$ represents an —N($R_{35}$)—Y—$R_{36}$ radical in which $R_{36}$ is a phenyl radical substituted by alkoxy.

This hydrolysis is generally carried out in an inert solvent, such as a chlorinated solvent (for example dichloromethane or chloroform), by means of boron tribromide at a temperature in the region of 20° C.

The compounds of formula (I) for which R represents a $CHR_{33}$ radical and $R_{33}$ represents an —N($R_{35}$)—Y—$R_{36}$ radical in which $R_{36}$ is a phenyl radical substituted by hydroxy(1C)alkyl can also be prepared by the action of diisobutylaluminum hydride on a corresponding compound of formula (I) for which $R_{33}$ represents an —N($R_{35}$)—Y—$R_{36}$ radical in which $R_{36}$ is a phenyl radical substituted by alkoxycarbonyl.

This reaction is generally carried out in an inert solvent, such as toluene, by means of diisopropylaluminum hydride at a temperature of between −50° C. and 25° C.

The compounds of formula (I) for which R represents a $CHR_{33}$ radical and $R_{33}$ represents an —N($R_{35}$)—Y—$R_{36}$ radical in which $R_{36}$ is a phenyl radical substituted by 1-pyrrolidinyl can also be prepared by reaction of pyrrolidine and of a corresponding compound of formula (I) for which $R_{33}$ represents an —N($R_{35}$)—Y—$R_{36}$ radical in which $R_{36}$ is a phenyl radical substituted by fluorine.

This reaction is preferably carried out in an inert solvent, such as dimethyl sulfoxide, at a temperature of 90° C.

The compounds of formula (I) for which R represents a $CHR_{46}$ radical and $R_{46}$ represents an —N($R_{47}$)$R_{48}$ in which $R_{48}$ is a hydrogen atom, —N($R_{47}$)—CO—$R_{48}$ or —N($R_{47}$)—SO$_2R_{49}$ radical, $R_{47}$ is a —C($R_{54}$)($R_{55}$)—Ar$_3$ or —C($R_{54}$)($R_{55}$)-Het$_3$ radical and $R_{55}$ is a hydrogen atom can be prepared according to the following reaction scheme:

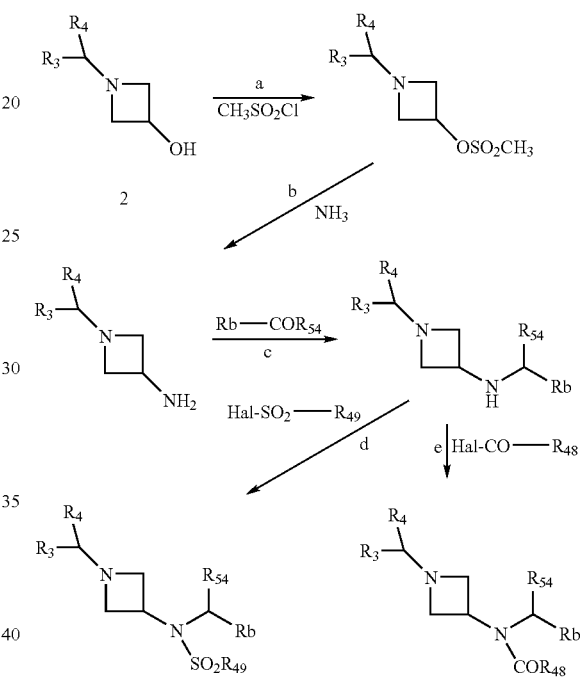

In these formulae, $R_4$, $R_3$, $R_{49}$ and $R_{54}$ have the same meanings as in the formula (I), Rb represents Ar$_3$ or Het$_3$ radical, Ar$_3$ and Het$_3$ having the same meanings as in the formula (I), and Hal represents a halogen atom and preferably chlorine or bromine.

Stage a is generally carried out in an inert solvent, such as tetrahydrofuran, dioxane or a chlorinated solvent (for example dichloromethane or chloroform), at a temperature of between 15 and 30° C. in the presence of a base, such as a trialkylamine (for example triethylamine or dipropylethylamine), or in pyridine at a temperature between 0 and 30° C.

Stage b is preferably carried out in methanol, in an autoclave, at a temperature of between 50 and 70° C.

Stage c is generally carried out in an inert solvent, such as a chlorinated solvent (for example dichloromethane), in the presence of sodium triacetoxyborohydride and acetic acid at a temperature in the region of 20° C.

Stages d and e are generally carried out in an inert solvent, such as tetrahydrofuran, dioxane or a chlorinated solvent (for example dichloromethane or chloroform), in the presence of an amine, such as a trialkylamine (for example triethylamine), at a temperature of between 5° C. and 20° C.

The Rb—COR$_{54}$ derivatives are commercially available or can be obtained according to the methods described, for example, by R. C. Larock, Comprehensive Organic Transformations, VCH editor.

The Hal-SO$_2$R$_{49}$ derivatives are commercially available or can be obtained by halogenation of the corresponding sulfonic acids, in particular in situ in the presence of chlorosulfonyl isocyanate and of alcohol, in a halogenated solvent (for example dichloromethane or chloroform).

These Hal-COR$_{48}$ derivatives are commercially available or can be prepared by halogenation of the corresponding carboxylic acids, in particular in situ in the presence of thionyl chloride, in an halogenated solvent (for example dichloromethane or chloroform).

The compounds of formula (I) for which R represents a CHR$_{46}$ radical and R$_{46}$ represents an —N(R$_{47}$)R$_{48}$ radical can be prepared according to the following reaction scheme:

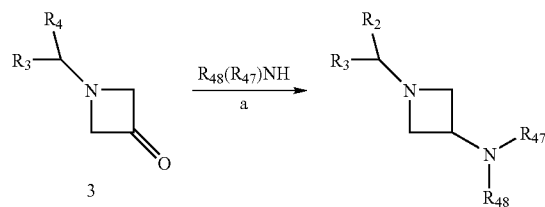

In these formulae, R$_4$, R$_3$, R$_{47}$ and R$_{48}$ have the same meanings as in the formula (I).

This reaction is generally carried out in an inert solvent, such as a chlorinated solvent (for example dichloromethane), in the presence of sodium triacetoxyborohydride and of acetic acid at a temperature in the region of 20° C.

The compounds HN(R$_{47}$)R$_{48}$ are commercially available or can be prepared according to conventional methods known to a person skilled in the art or by application or adaptation of the methods described by Park K. K. et al., J. Org. Chem., 60 (19), 6202 (1995); Kalir A. et al., J. Med. Chem., 12 (3), 473 (1969); Sarges R., J. Org. Chem., 40 (9), 1216 (1975); Zaugg H. E., J. Org. Chem., 33 (5), 2167 (1968); Med. Chem., 10, 128 (1967); J. Am. Chem. Soc., 2244 (1955); Chem. Ber., 106, 2890 (1973); Chem. Pharm. Bull., 16 (10), 1953 (1968); Bull. Soc. Chim. Fr., 835 (1962).

The azetidinones 3 can be obtained by oxidation of the corresponding azetidinols 2, preferably in dimethyl sulfoxide, by means of the sulfur trioxide-pyridine complex at a temperature in the region of 20° C. or by means of dimethyl sulfoxide, in the presence of oxalyl chloride and of triethylamine, at a temperature of between −70° C. and −50° C.

The compounds of formula (I) for which R represents a CHR$_{46}$ radical and R$_{46}$ represents an —N(R$_{47}$)COR$_{48}$ or —N(R$_{47}$)SO$_2$R$_{49}$ radical can be prepared according to the following reaction scheme:

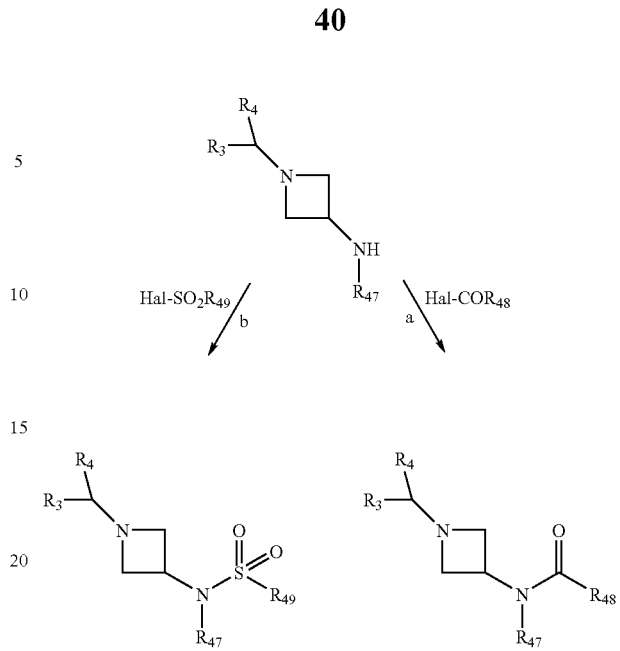

In these formulae, R$_4$, R$_3$, R$_{47}$, R$_{48}$ and R$_{49}$ have the same meanings as in the formula (I) and Hal represents a halogen atom and preferably chlorine.

Stages a and b are generally carried out in an inert solvent, such as tetrahydrofuran, dioxane or a chlorinated solvent (for example dichloromethane or chloroform), in the presence of an amine, such as a trialkylamine (for example triethylamine), at a temperature of between 5° C. and 20° C.

The compounds of formula (I) for which R represents a CHR$_{46}$ radical and R$_{46}$ represents an —N(R$_{47}$)—SO$_2$—R$_{49}$ radical for which R$_{47}$ is a Het$_3$ or Ar$_3$ radical can be prepared according to the following reaction scheme:

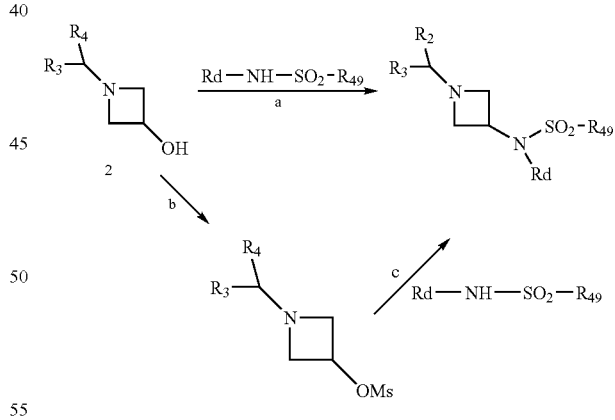

In these formulae, R$_4$, R$_3$ and R$_{49}$ have the same meanings as in the formula (I), Rd represents an Ar$_3$ or Het$_3$ radical (Het$_3$ and Ar$_3$ having the same meanings as in the formula (I)) and Ms represents a methylsulfonyloxy radical.

Stage a is generally carried out in an inert solvent, such as tetrahydrofuran, in the presence of triphenylphosphine and of diethyl azodicarboxylate at a temperature of between 0° C. and the boiling temperature of the reaction medium.

Stage b is generally carried out in an inert solvent, such as tetrahydrofuran, dioxane or a chlorinated solvent (for example dichloromethane or chloroform), at a temperature of between 15° C. and 30° C. in the presence of a base, such as a trialkylamine (for example triethylamine or dipropylethylamine), or in pyridine at a temperature between 0° C. and 30° C.

Stage c is preferably carried out in an inert solvent, such as dioxane, in the presence of $CsCO_3$ at reflux temperature of the reaction mixture.

The derivatives for which Rd represents an N-oxidized nitrogenous heterocycle can be reduced to nonoxidized compound according to the method described by Sanghanel E. et al., Synthesis, 1375 (1996).

The $Rd-NH-SO_2R_{49}$ derivatives can be obtained according to the following reaction scheme:

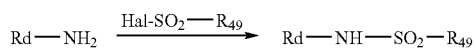

In these formulae, Hal represents a halogen atom and Rd represents a $Het_3$ or $Ar_3$ radical. The reaction is carried out in an inert solvent, such as tetrahydrofuran, dioxane or a chlorinated solvent (for example dichloromethane or chloroform), at a temperature of between 15° C. and 30° C. in the presence of a base, such as a trialkylamine (for example triethylamine or dipropylethylamine), or in pyridine at a temperature of between 0° C. and 30° C.

The derivatives for which Rd represents an N-oxidized nitrogenous heterocycle can be obtained according to methods described by Rhie R., Heterocycles, 41 (2), 323 (1995).

The compounds of formula (I) for which R represents a $CHR_{46}$ radical and $R_{46}$ represents an $-N(R_{47})-SO_2-R_{49}$ radical for which $R_{47}$ is a piperidin-4-yl radical optionally substituted on the nitrogen by an alkyl radical can also be prepared according to the following reaction scheme:

In these formulae, $R_4$, $R_3$ and $R_{49}$ have the same meanings as in the formula (I), alk represents an alkyl radical and Re represents a tert-butylcarbonyloxy radical.

Stage a is carried out in an inert solvent, such as a chlorinated solvent (for example dichloromethane), in the presence of a hydride, such as sodium triacetoxyborohydride, and acetic acid at a temperature of between 0° C. and the boiling temperature of the reaction medium.

Stage b is generally carried out in an inert solvent, such as tetrahydrofuran, dioxane or a chlorinated solvent (for example dichloromethane or chloroform), in the presence of an amine, such as a trialkylamine (for example triethylamine), at a temperature of between 5° C. and 20° C.

Stage c is carried out by means of hydrochloric acid in dioxane at a temperature of between 0° C. and the boiling temperature of the reaction medium.

Stage d is carried out by any means known to a person skilled in the art for alkylating an amine without affecting the remainder of the molecule. Use may be made, for example, of an alkyl halide in the presence of an organic base, such as triethylamine, or an alkali metal hydroxide (for example sodium hydroxide or potassium hydroxide), optionally in the presence of tetrabutylammonium bromide, in an inert solvent, such as dimethyl sulfoxide, dimethylformamide or pyridine, at a temperature of between 20 and 50° C.

The compounds of formula (I) for which R represents a $CHR_{46}$ radical and $R_{46}$ represents an $-N(R_{47})-SO_2-R_{49}$ radical for which $R_{47}$ is a phenyl radical substituted by a pyrrolidin-1-yl radical can also be prepared by reaction of pyrrolidine with a corresponding compound of formula (I) for which $R_{46}$ represents a $-N(R_{47})SO_2R_{49}$ radical for which $R_{47}$ is a phenyl radical substituted by a halogen atom.

This reaction is preferably carried out in dimethyl sulfoxide at a temperature of between 50 and 95° C.

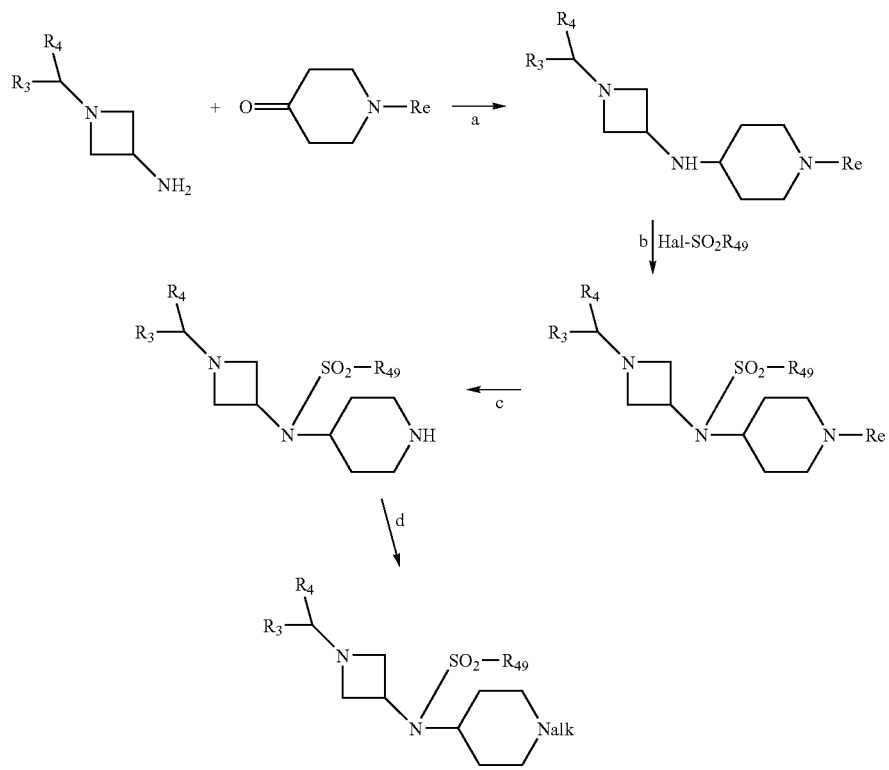

It is understood for the person skilled in the art that, in order to carry out the processes according to the invention described above, it may be necessary to introduce protective groups for the amino, hydroxyl and carboxyl functional groups in order to prevent side reactions. These groups are those which make it possible to be removed without affecting the remainder of the molecule. Mention may be made, as examples of protective groups for the amino functional group, of tert-butyl or methyl carbamates, which can be regenerated by means of iodotrimethylsilane, or allyl carbamates, by means of palladium catalysts. Mention may be made, as examples of protective groups for the hydroxyl functional group, of triethylsilyl and tert-butyldimethylsilyl, which can be regenerated by means of tetrabutylammonium fluoride, or asymmetric acetals (for example methoxymethyl or tetrahydropyranyl), with regeneration by means of hydrochloric acid. Mention may be made, as protective groups for the carboxyl functional groups, of esters (for example allyl or benzyl), oxazoles and 2-alkyl-1,3-oxazolines. Other protective groups which can be used are described by Greene T. W. et al., Protecting Groups in Organic Synthesis, second edition, 1991, John Wiley & Sons.

The compounds of formula (I) can be purified by the usual known methods, for example by crystallization, chromatography or extraction.

The enantiomers or the compounds of formula (I) can be obtained by resolution of the racemates, for example by chromatography on a chiral column according to Pirckle W. H. et al., Asymmetric Synthesis, vol. 1, Academic Press (1983), or by formation of salts or by synthesis from chiral precursors. The diastereoisomers can be prepared according to known conventional methods (crystallization, chromatography or starting from chiral precursors).

Mention may be made, as examples of pharmaceutically acceptable salts of the following salts: benzenesulfonate, hydrobromide, hydrochloride, citrate, ethanesulfonate, fumarate, gluconate, iodate, isethionate, maleate, methanesulfonate, methylenebis(β-oxynaphthoate), nitrate, oxalate, pamoate, phosphate, salicylate, succinate, sulfate, tartrate, theophyllineacetate and p-toluenesulfonate.

EXAMPLE 1

N-{1-[Bis(4-chlorophenyl)methyl]azetidin-3-yl}-N-(pyrid-3-yl)methylsulfonamide can be prepared by carrying but the preparation in the following way: 0.042 cm$^3$ of phosphorus trichloride is added to a solution of 0.144 g of N-{1-[bis(4-chlorophenyl)-methyl]azetidin-3-yl}-N-(1-oxidopyrid-3-yl)methyl-sulfonamide in 5 cm$^3$ of chloroform and then the mixture is heated to the reflux temperature. After stirring for 1 hour 30 minutes, the reaction mixture is allowed to return to normal temperature, 5 cm$^3$ of 0.1N hydrochloric acid are then added to the mixture, and then the mixture is stirred and separated by settling. The organic phase is diluted with 20 cm$^3$ of chloroform, dried over magnesium sulfate, filtered and then concentrated to dryness under reduced pressure (2.7 kPa). The residue is chromatographed on a column of silica gel (particle size 0.063–0.200 mm, height 9 cm, diameter 1.8 cm), elution being carried out under a pressure of 0.1 bar of argon with a mixture of dichloromethane and of methanol (95/5 by volume) and 15-cm$^3$ fractions being collected. Fractions 2 to 4 are combined and concentrated to dryness under reduced pressure (2.7 kPa). The residue is stirred with 15 cm$^3$ of diethyl ether, the suspension is filtered and the solid is pulled dry and then dried under reduced pressure (2.7 kPa). 35 mg of N-{1-[bis(4-chloro-phenyl)-methyl]azetidin-3-yl}-N-(pyrid-3-yl)methyl-sulfonamide are obtained in the form of a cream solid [$^1$H N.M.R. spectrum (300 MHz, CDCl$_3$, δ in ppm): from 2.80 to 2.95 (mt, 2H), 2.87 (s, 3H), 3.51 (split t, J=7 and 1.5 Hz, 2H), 4.18 (s, 1H), 4.65 (mt, 1H), from 7.15 to 7.35 (mt, 8H), 7.37 (broad dd, J=8 and 5 Hz, 1H), 7.64 (reduced d, J=8 Hz, 1H), 8.52 (broad d, J=2 Hz, 1H), 8.61 (broad d, J=5 Hz, 1H)].

EXAMPLE 2

Method 1:

N-{1-[Bis(4-chlorophenyl)methyl]azetidin-3-yl}-N-(3,5-difluorophenyl)methylsulfonamide can be prepared by carrying out the preparation in the following way: 1.0 g of cesium carbonate is added to a mixture of 1.23 g of 1-[bis(4-chlorophenyl)methyl]-azetidin-3-yl}methylsulfonate and of 0.66 g of N-(3,5-difluorophenyl)methylsulfonamide in 25 cm$^3$ of dioxane. After stirring for 5 hours at the reflux temperature and then for 20 hours at 20° C., 50 cm$^3$ of diethyl ether and 30 cm$^3$ of brine are added to the reaction mixture and then the reaction mixture is stirred and separated by settling. The organic phase is dried over magnesium sulfate, filtered and then concentrated to dryness at 50° C. under reduced pressure (2.7 kPa). The orange oil obtained is chromatographed on a column of silica gel (particle size 0.040–0.063 mm, height 25 cm, diameter 2.0 cm), elution being carried out under a pressure of 0.5 bar of argon with a mixture of cyclohexane and of ethyl acetate (65/35 by volume) and 10-cm$^3$ fractions being collected. Fractions 6 to 10 are combined and concentrated to dryness under reduced pressure (2.7 kPa). The residue is chromatographed on a column of silica gel (particle size 0.040–0.063 mm, height 15 cm, diameter 1.0 cm), elution being carried out under a pressure of 0.5 bar of argon with a mixture of cyclohexane and of ethyl acetate (65/35 by volume) and 5-cm$^3$ fractions being collected. Fraction 7 is concentrated to dryness under reduced pressure (2.7 kPa). 0.11 g of N-{1-[bis(4-chlorophenyl)methyl]-azetidin-3-yl}-N-(3,5-difluorophenyl)methylsulfonamide is obtained in the form of a white powder [$^1$H N.M.R. spectrum (300 MHz, CDCl$_3$, δ in ppm): 2.82 (s, 3H), 2.85 (mt, 2H), 3.52 (split t, J=7 and 2 Hz, 2H), 4.22 (s, 1H), 4.47 (mt, 1H), from 6.75 to 6.90 (mt, 3H), from 7.20 to 7.35 (mt, 8H)].

Method 2:

0.78 cm$^3$ of diethyl azodicarboxylate and 1.31 g of triphenylphosphine are added under argon to a solution of 1.41 g of 1-[bis(4-chlorophenyl)methyl]-azetidin-3-ol and of 0.95 g of N-(3,5-difluorophenyl)-methylsulfonamide in 100 cm$^3$ of anhydrous tetrahydrofuran. After stirring for 16 hours at 20° C., 300 cm$^3$ of ethyl acetate are added and the reaction mixture is washed twice with 100 cm$^3$ of water, dried over magnesium sulfate and concentrated to dryness under reduced pressure (2.7 kPa). The residue is chromatographed on a column of silica gel (particle size 0.20–0.063 mm, height 50 cm, diameter 4 cm), elution being carried out under a pressure of 0.6 bar of argon with a mixture of cyclohexane and of ethyl acetate (75/25 by volume) and 125-cm$^3$ fractions being collected. Fractions 6 to 12 are combined and concentrated to dryness under reduced pressure (2.7 kPa). 1.8 g of a solid are obtained, which solid is dissolved under hot conditions in an ethyl acetate/diisopropyl ether mixture (15/2 by volume), cooled and diluted with 100 cm$^3$ of pentane to initiate crystallization. After filtration and drying, 1.0 g of N-{1-[bis(4-chlorophenyl)methyl]azetidin-3-yl}-N-(3,5-difluorophenyl)methylsulfonamide is obtained in the form of white crystals melting at 154° C.

N-(3,5-Difluorophenyl)methylsulfonamide can be prepared by carrying out the preparation in the following way: 2.0 cm$^3$ of methylsulfonyl chloride, 3.8 cm$^3$ of triethylamine and 20 mg of 4-dimethylamino-pyridine are slowly added to a solution of 3.5 g of 3,5-difluoroaniline in 75 cm$^3$ of dichloromethane. After stirring for 20 hours at 20° C., the reaction mixture, to which 20 cm$^3$ of dichloromethane and 20 cm$^3$ of water are added, is stirred and then separated by settling. The organic phase is dried over magnesium sulfate, filtered and then concentrated to dryness under reduced pressure (2.7 kPa). The residue is chromatographed on a column of silica gel (particle size 0.063–0.200 mm, height 20 cm, diameter 2.0 cm), elution being carried out under a pressure of 0.1 bar of argon with dichloromethane and 25-cm$^3$ fractions being collected. Fractions 14 to 20 are combined and concentrated to dryness under reduced pressure (2.7 kPa). 0.66 g of N-(3,5-difluorophenyl)methylsulfonamide is obtained in the form of a white powder.

1-[Bis(4-chlorophenyl)methyl]azetidin-3-yl methylsulfonate can be prepared by carrying out the preparation in the following way: 3.5 cm$^3$ of methylsulfonyl chloride are added under argon over 10 minutes to a solution of 12 g of 1-[bis(4-chloro-phenyl)methyl]azetidin-3-ol in 200 cm$^3$ of dichloromethane, then the mixture is cooled to +5° C. and 3.8 cm$^3$ of pyridine are added in over 10 minutes. After stirring for 30 minutes at +5° C. and then for 20 hours at 20° C., the reaction mixture is diluted with 100 cm$^3$ of water and 100 cm$^3$ of dichloromethane. The mixture, filtered first, is separated by settling. The organic phase is washed with water and then dried over magnesium sulfate, filtered and concentrated to dryness under reduced pressure (2.7 kPa). The oil obtained is chromatographed on a column of silica gel (particle size 0.063–0.200 mm, height 40 cm, diameter 3.0 cm), elution being carried out under a pressure of 0.5 bar of argon with a mixture of cyclohexane and of ethyl acetate (70/30 by volume) and 100-cm$^3$ fractions being collected. Fractions 4 to 15 are combined and concentrated to dryness under reduced pressure (2.7 kPa). 6.8 g of 1-[bis(4-chlorophenyl)methyl]-azetidin-3-yl methylsulfonate are obtained in the form of a yellow oil.

1-[Bis(4-chlorophenyl)methyl]azetidin-3-ol can be prepared according to the procedure described by Katritzky A. R. et al., J. Heterocycl. Chem., 271 (1994), starting from 35.5 g of [bis(4-chlorophenyl)-methyl]amine hydrochloride and 11.0 cm$^3$ of epichlorohydrin. 9.0 g of 1-[bis(4-chlorophenyl)-methyl]azetidin-3-ol are isolated.

[Bis(4-chlorophenyl)methyl]amine hydrochloride can be prepared according to the method described by Grisar M. et al., J. Med. Chem., 885 (1973).

The synergistic effect of the combination of one or more products which activate dopaminergic neurotransmission in the brain and of one or more CB1 antagonists in the treatment of Parkinson's disease was determined in a model of akinesia induced by reserpine in the rat according to the following protocol:

Male Sprague-Dawley rats were treated with reserpine administered subcutaneously at a dose of 3 mg/kg (1 ml/kg) in order to induce akinesia in the animal. 18 hours after this treatment, the locomotor activity of these animals was measured and recorded using an automatic system (Videotrack, France). The locomotion, expressed in centimeters, is estimated by a mean overall distance covered during this period (n=11–38 rats per group). The statistical analysis is carried out by variance analysis and a post-hoc comparison (if appropriate) using a Mann-Whitney or Dunnett test. A significant effect is recorded for p<0.05.

The synergistic effect of the combination is demonstrated in Tables 1 and 2.

Table 1 relates to the ip administration of the CB1 antagonist and Table 2 relates to the po administration of the CB1 antagonist.

The results for the ip administration of the CB1 antagonist (Table 1) are expressed as percentage of increase with respect to the activity of quinpirole and as percentage of decrease with respect to the activity of a very strong dose of levodopa.

The combination of a CB1 receptor antagonist and of a D2 dopaminergic agonist (quinpirole) is produced in the following way:

The CB1 antagonist product (1.5 mg/kg i.p., 2 ml/kg) and quinpirole (62.5 µg/kg i.p., 1 ml/kg) are coadministered 18 hours after the injection of reserpine. The recording of the motor activity begins 5 minutes after the co-administration of the products and lasts 1 hour.

The combination of the CB1 receptor antagonist and of a strong dose of levodopa (dyskinesia model) is produced in the following way:

The CB1 antagonist product (3 mg/kg i.p., 2 ml/kg) and levodopa (120 mg/kg+benserazide, 50 mg/kg i.p., 5 ml/kg) are co-administered. Benserazide is a peripheral dopa-decarboxylase inhibitor which allows levodopa to cross the hematoencephalic barrier before its conversion into dopamine. The recording of the motor activity begins 5 minutes after the co-administration and lasts 2.5 hours.

TABLE 1

| Reserpine-treated rats | Combination with quinpirole (62.5 µg/kg ip) | Combination with levodopa (120 mg/kg ip) |
| --- | --- | --- |
| Example 2 | +139%*** (1.5 mg/kg i.p.) | −54% NS (3 mg/kg i.p.) |
| Example 1 | +96%** | −20% NS (1.5 mg/kg) (3 mg/kg untested) |
| SR141716A 1 mg/kg i.p. | +116%*** | −61%* |

SR141716A: N-(piperidin-1-yl)-5-(4-chlorophenyl)-1-(2,4-dichlorophenyl)-4-methyl-1H-pyrazole-3-carboxamide hydrochloride ANOVA+Mann-Whitney: *p<0.05, p<0.01, *p<0.001.

These results according to the invention show that the CB1 receptor antagonists:
significantly potentiate the effects of a D2 dopaminergic agonist (reduction in the symptoms of Parkinson's disease)
and reduce the hyperactivity induced by a very strong dose of levodopa (antidyskinetic activity).

The studies by the oral route are carried out in a hydrophobic formulation solvent Labrafil/Labrasol (40/60%, w/w). These products are administered (in a volume of 1 ml/kg) one hour before the dopaminergic agonist. The recording of the locomotor activity begins 5 min after the intraperitoneal injection of the dopaminergic agonist and lasts 1 hour. The D1 dopaminergic agonist is 0.3 mg/kg C1-APB. The D2 dopaminergic agonist is 0.1 mg/kg quinpirole.

The results for the po administration of the CB1 antagonist at three different doses (1, 3 and 10 mg/kg/po) (Table 2)

are expressed as percentage of increase with respect to the activity of quinpirole and a percentage of decrease with respect to the activity of a strong dose of C1-APB (SKF 82958).

TABLE 2

| | Dose mg/kg po | Combination with quinpirole (0.1 mg/kg ip) | Combination with C1-APB (0.3 mg/kg ip) |
|---|---|---|---|
| Example 2 | 1 | +55% NS | −16% NS |
| | 3 | +62%* | −61%* |
| | 10 | +97%** | −62%* |
| Example 1 | 1 | −1% NS | +22% NS |
| | 3 | +101%* | −21% NS |
| | 10 | +102%* | −53%* |
| SR141716A | 1 | +57%* NS | −32% NS |
| | 3 | +121%** | −58%* |
| | 10 | +87%** | −82%** |

SR141716A: N-(piperidin-1-yl)-5-(4-chlorophenyl)-1-yl)-(2,4-dichlorophenyl)-4-methyl-1H-pyrazole-3-carboxamide hyrochloride ANOVA+DUNNETT: *$p$<0.05, **$p$<0.01

These results according to the invention show that the CB1 receptor antagonists:
significantly potentiate the effects of a D2 dopaminergic agonist (reduction in the symptoms of Parkinson's disease)
and reduce the hyperactivity induced by a strong dose of D1 type (antidyskinetic activity).

The compounds of the combination can be employed orally, parenterally, transdermally or rectally, either simultaneously or separately or spread out over time.

The present invention also relates to the pharmaceutical compositions comprising the combination of one or more products which activate neurotransmission in the brain and of one or more CB1 receptor antagonists as defined above with a pharmaceutically acceptable vehicle.

Use may be made, as solid compositions for oral administration, of tablets, pills, powders (hard gelatin capsules, cachets) or granules. In these compositions, the active principles are mixed with one or more inert diluents, such as starch, cellulose, sucrose, lactose or silica, under an argon stream. These compositions can also comprise substances other than the diluents, for example one or more lubricants, such as magnesium stearate or talc, a colorant, a coating (dragees) or a glaze.

Use may be made, as liquid compositions for oral administration, of pharmaceutically acceptable solutions, suspensions, emulsions, syrups and elixirs comprising inert diluents, such as water, ethanol, glycerol, vegetable oils or liquid paraffin. These compositions can comprise substances other than the diluents, for example wetting, sweetening, thickening, flavoring or stabilizing products.

The sterile compositions for parenteral administration can preferably be solutions in aqueous or nonaqueous form, suspensions or emulsions. Use may be made, as solvent or vehicle, of water, propylene glycol, a polyethylene glycol, vegetable oils, in particular olive oil, injectable organic esters, for example ethyl oleate, or other suitable organic solvents. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which comprise, in addition to the active product, excipients such as cocoa butter, semisynthetic glycerides or polyethylene glycols.

The pharmaceutical compositions including the combination as defined above generally comprise 0.1 to 500 mg of the CB1 antagonist. The present invention also relates to the method for the treatment of Parkinson's disease which consists in administering, to the patient, a combination or a pharmaceutical composition including the combination as defined above, either simultaneously or separately or spread out over time.

The doses depend on the desired effect, on the duration of treatment and on the administration route used; they are generally from 0.1 to 500 mg of the CB1 antagonist per day by the oral route for an adult.

Generally, the doctor will determine the appropriate dosage according to the age, weight and any other factors specific to the subject to be treated.

What is claimed is:
1. A composition comprising a dopaminergic agonist and of one or more CB1 antagonist azetidine derivatives of formula I:

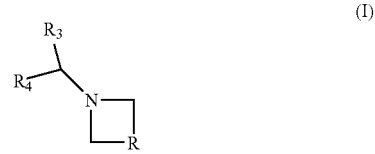

wherein
either A:
R is $CR_1R_2$, $C=C(R_5)SO_2R_6$ or $C=C(R_7)SO_2$alk;
wherein either $R_1$ is hydrogen and $R_2$ is —$C(R_8)(R_9)(R_{10})$, —$C(R_8)(R_{11})(R_{12})$, —CO—$NR_{13}R_{14}$, —$CH_2$—CO—$NR_{13}R_{14}$, —$CH_2$—CO—$R_6$, —CO—$R_6$, —CO-cycloalkyl, —SO—$R_6$, —$SO_2$—$R_6$, —$C(OH)(R_{12})(R_6)$, —$C(OH)(R_6)$(alkyl), —$C(=NOalk)R_6$, —$C(=NO-CH_2-CH=CH_2)R_6$, —$CH_2$—$CH(R_6)NR_{31}R_{32}$, —$CH_2$—$C(=NOalk)R_6$, —$CH(R_6)NR_{31}R_{32}$, —$CH(R_6)NHSO_2$alk, —$CH(R_6)NHCON$-Halk or —$CH(R_6)NHCO$alk; or
$R_1$ is alkyl, NH—$R_{15}$, cyano, —S-alk-$NR_{16}R_{17}$, —$CH_2$—$NR_{18}R_{19}$ or —$NR_{20}R_{21}$; and
$R_2$ is —$C(R_8)(R_{11})(R_{12})$;
$R_3$ and $R_4$, which are identical or different, independently are either alkyl, cycloalkyl, aryl chosen from phenyl, naphthyl or indenyl, wherein aryl being unsubstituted or substituted by one or more halogen, alkyl, alkoxy, formyl, hydroxyl, trifluoromethyl, trifluoromethoxy, —CO-alk, cyano, —COOH, —COOalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl or -alk-$NR_{24}R_{25}$; or heteroaryl chosen from benzofuryl, benzothiazolyl, benzothienyl, benzoxazolyl, chromanyl, 2,3-dihydroxybenzofuryl, 2,3-dihydrobenzothienyl, furyl, imidazolyl, isochromanyl, isoquinolyl, pyrrolyl, pyridyl, pyrimidinyl, quinolyl, 1,2,3,4-tetrahydroisoquinolyl, thiazolyl and thienyl, wherein heteroaryl is unsubstituted or substituted by one or more halogen, alkyl, alkoxy, hydroxyl, trifluoromethyl, trifluorometrhoxy, cyano, —COOH, —COOalk, —CO—NH—NR$_{24}$R$_{25}$, —CONR$_{22}$R$_{23}$, -alk-NR$_{24}$R$_{25}$, alkylsulfanyl, alkylsulfinyl, alkylsulfonyl, alkylsulfanylalkyl, alkylsulfinylalkyl, alkylsulfonylalkyl or hydroxyalkyl;

$R_5$ is hydrogen or alkyl;

$R_6$ is $Ar_1$ or $Het_1$;

$R_7$ is cycloalkyl, heterocycloalkyl or heterocyclenyl optionally substituted by —CSO-phenyl;

$R_8$ is hydrogen or alkyl;

$R_9$ is —CO—NR$_{26}$R$_{27}$, —COOH, —COOalk, —CH$_2$OH, —NH—CO—NH-alk, —CH$_2$—NHR$_{28}$ or —NHCOOalk;

$R_{10}$ is $Ar_1$ or $Het_1$;

$R_{11}$ is —SO$_2$-alk, —SO$_2$—$Ar_1$ or —SO$_2$-$Het_1$;

$R_{12}$ is hydrogen, $Ar_1$ or $Het_1$;

$R_{13}$ is hydrogen or alkyl;

$R_{14}$ is $Ar_1$, $Het_1$, -alk-$Ar_1$ or -alk-$Het_1$;

$R_{15}$ is alkyl, cycloalkyl or -alk-NR$_{29}$R$_{30}$;

$R_{16}$ and $R_{17}$, which are identical or different, independently are either hydrogen or alkyl; or $R_{16}$ and $R_{17}$ taken together with the nitrogen atom to which they are attached form a saturated or unsaturated 3 to 10 ring membered mono- or 5 to 10 ring membered bicyclic heterocycle, optionally comprising one or more other heteroatoms chosen from oxygen, sulfur and nitrogen and optionally substituted by one or more alkyl;

$R_{18}$ is hydrogen or alkyl;

$R_{19}$ is hydrogen, alkyl, cycloalkyl, cycloalkylalkyl, cycloalkylcarbonyl, —SO$_2$alk, —CO—NHalk or —COOalk; or $R_{18}$ and $R_{19}$ taken with the nitrogen atom to which they are attached form a saturated or unsaturated 3 to 10 ring membered mono- or 5 to 10 ring membered bicyclic heterocycle, optionally comprising one or more heteroatoms chosen from oxygen, sulfur and nitrogen and optionally substituted by one or more alkyl;

—NR$_{20}$R$_{21}$ is a saturated or unsaturated monocyclic heterocycle having 3 to 8 ring members and optionally comprising another heteroatom chosen from oxygen, nitrogen and sulfur;

$R_{22}$ and $R_{23}$, which are identical or different, independently are hydrogen or alkyl; or $R_{22}$ and $R_{23}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one more alkyl;

$R_{24}$ and $R_{25}$, which are identical or different, independently are hydrogen, alkyl, —COOalk, cycloalkyl, alkylcycloalkyl, -alk-O-alk or hydroxyalkyl; or $R_{24}$ and $R_{25}$ taken together with the nitrogen atom to which they are attached form a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$;

$R_{26}$ and $R_{27}$, which are identical or different, independently are hydrogen, alkyl, hydroxyalkyl, cycloalkyl, cycloalkylalkyl, -alk-COOalk, -alk-$Ar_1$, alk-$Het_1$, $Het_1$, or -alk-N(alk)$_2$; or $R_{26}$ and $R_{27}$ taken together with the nitrogen atom to which they are attached form a saturated or unsaturated and mono- or bicyclic heterocycle having 3 to 10 ring members and optionally comprising one or more heteroatoms chosen from oxygen, sulfur and nitrogen and optionally substituted by one or more alkyl, alkoxy or halogen;

$R_{28}$ is —CH$_2$-alk, benzyl, —SO$_2$alk, —CONHalk, —COalk, cycloalkylalkylcarbonyl, cycloalkylcarbonyl or —CO—(CH$_2$)$_n$OH, wherein n is an integer from 1 to 3;

$R_{29}$ and $R_{30}$, which are identical or different, independently are hydrogen or alkyl; or $R_{29}$ and $R_{30}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl radicals;

$R_{31}$ and $R_{32}$, which are identical or different, independently are hydrogen, alkyl, $Ar_1$ or -alk-$Ar_1$; or $R_{31}$ and $R_{32}$ taken together with the nitrogen atom to which they are attached form a heterocycle chosen from aziridinyl, azetidinyl, pyrrolidinyl and piperidinyl;

$Ar_1$ is phenyl or naphthyl optionally substituted by one or more substituents chosen from halogen, alkyl, alkoxy, —CO-alk, cyano, —COOH, —COOalk, —CONR$_{22}$R$_{23}$, —CO—NH—NR$_{24}$R$_{25}$, alkylsulfanyl, alkylsulfinyl, alkylsulfonyl, alkylsulfanylalkyl, alkylsulfinylalkyl, alkylsulfonylalkyl, hydroxyalkyl, -alk-NR$_{24}$R$_{25}$, —NR$_{24}$R$_{25}$, alkylthioalkyl, formyl, hydroxyl, CF$_3$, OCF$_3$, $Het_1$, O-alk-NH-cycloalkyl or SO$_2$NH$_2$;

$Het_1$ is a saturated or unsaturated and mono- or bicyclic heterocycle having 3 to 10 ring members and comprising one or more heteroatoms chosen from oxygen, sulfur and nitrogen and optionally substituted by one or more halogen, alkyl, alkoxy, alkoxycarbonyl, —CONR$_{22}$R$_{23}$, hydroxyl, hydroxyalkyl, oxo or SO$_2$NH$_2$;

or B: wherein

R is CHR$_{33}$; wherein $R_{33}$ is —NHCOR$_{34}$ or —N(R$_{35}$)—Y—R$_{36}$;

Y is CO or SO$_2$;

$R_3$ and $R_4$, which are identical or different, are either aryl chosen from phenyl, naphthyl and indenyl, wherein aryl being unsubstituted or substituted by one or more halogen, alkyl, alkoxy, formyl, hydroxyl, trifluoromethyl, trifluoromethoxy, —CO-alk, cyano, —COOH, —COOalk, —CONR$_{37}$R$_{38}$, —CO—NH—NR$_{39}$R$_{40}$, alkylsulfanyl, alkylsulfinyl, alkylsulfonyl, alkylsulfanylalkyl, alkylsulfinylalkyl, alkylsulfonylalkyl, hydroxyalkyl or -alk-NR$_{37}$R$_{38}$; or heteroaryl chosen from benzofuryl, benzothiazolyl, benzothienyl, benzoxazolyl, chromanyl, 2,3-dihydro-benzofuryl, 2,3-dihydro-benzothienyl, pyrimidinyl, furyl, imidazolyl, isochromanyl, isoquinolyl, pyrrolyl, pyridyl, quinolyl, 1,2,3,4-tetrahydroisoquinolyl, thiazolyl and thienyl, wherein heteroaryl being unsubstituted or substituted by halogen, alkyl, alkoxy, hydroxyl, trifluoromethyl, trifluoromethoxy, cyano, —COOH, —COOalk, —CO—NH—NR$_{39}$R$_{40}$, —CONR$_{37}$R$_{38}$, -alk-NR$_{39}$R$_{40}$, alkylsulfanyl, alkylsulfinyl, alkylsulfonyl, alkylsulfanylalkyl, alkylsulfinylalkyl, alkylsulfonylalkyl or hydroxyalkyl;

$R_{34}$ is -alk-SO$_2$—R$_{41}$, -alk-SO$_2$—CH=CH—R$_{41}$, $Het_2$ substituted by —SO$_2$—R$_{41}$ or phenyl substituted by —SO$_2$—R$_{41}$ or -alk-SO$_2$—R$_{41}$;

$R_{35}$ is hydrogen or alkyl;

$R_{36}$ is phenylalkyl, $Het_2$ or $Ar_2$;

$R_{37}$ and $R_{38}$, which are identical or different, independently are hydrogen or alkyl; or $R_{37}$ and $R_{38}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl;

$R_{39}$ and $R_{40}$, which are identical or different, independently are hydrogen or alkyl, —COalk, cycloalkyl, alkylcycloalkyl, -alk-O-alk or hydroxyalkyl; or $R_{39}$ and $R_{40}$ taken together with the nitrogen atom to which they are attached form a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$;

$R_{41}$ is alkyl, $Ar_2$ or $Het_2$;

$Ar_2$ is phenyl, naphthyl or indenyl radical, these radicals optionally being substituted by one or more halogen, alkyl, alkoxy, cyano, —CO-alk, —COOH, —COOalk, —CONR$_{42}$R$_{43}$, —CO—NH—NR$_{44}$R$_{45}$, alkylsulfanyl, alkylsulfinyl, alkylsulfonyl, -alk-NR$_{44}$R$_{45}$, —NR$_{44}$R$_{45}$, alkylthioalkyl, formyl, hydroxyl, hydroxyalkyl, Het$_2$, —O-alk-NH-cycloalkyl, OCF$_3$, CF$_3$, —NH—CO-alk, —SO$_2$NH$_2$, —HN—COCH$_3$, —NH—COOalk or Het$_2$ or else on two adjacent carbon atoms by a dioxymethylene;

$Het_2$ is a saturated or unsaturated and mono- or bicyclic heterocycle having 3 to 10 ring members and comprising one or more heteroatoms chosen from oxygen, sulfur and nitrogen optionally substituted by one or more alkyl, alkoxy, vinyl, halogen, alkoxycarbonyl, oxo, hydroxyl, OCF$_3$ or CF$_3$, the nitrogenous heterocycles optionally being in their N-oxidized form;

$R_{42}$ and $R_{43}$, which are identical or different, independently are hydrogen or alkyl; or $R_{42}$ and $R_{43}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl;

$R_{44}$ and $R_{45}$, which are identical or different, independently are hydrogen, alkyl, —COOalk, cycloalkyl, alkylcycloalkyl, -alk-O-alk or hydroxyalkyl; or $R_{44}$ and $R_{45}$ taken together with the nitrogen atom to which they are attached form a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$;

or C: wherein

R is CHR$_{46}$, wherein $R_{46}$ is —N(R$_{47}$)R$_{48}$, —N(R$_{47}$)—CO—R$_{48}$ or —N(R$_{47}$)—SO$_2$R$_{49}$;

$R_3$ and $R_4$, which are identical or different, represent either an aryl chosen from phenyl, naphthyl and indenyl, wherein aryl being unsubstituted or substituted by one or more halogen, alkyl, alkoxy, formyl, hydroxyl, trifluoromethyl, trifluoromethoxy, —CO-alk, cyano, —COOH, —COOalk, —CONR$_{50}$R$_{51}$, —CO—NH—NR$_{52}$R$_{53}$, alkylsulfanyl, alkylsulfinyl, alkylsulfonyl, alkylsulfanylalkyl, alkylsulfinylalkyl, alkylsulfonylalkyl, hydroxyalkyl or -alk-NR$_7$R$_8$; or a heteroaryl chosen from benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl, wherein heteroaryl being unsubstituted or substituted by halogen, alkyl, alkoxy, hydroxyl, trifluoromethyl, trifluoromethoxy, cyano, —COOH, —COOalk, —CO—NH—NR$_{52}$R$_{53}$, —CONR$_{50}$R$_{51}$, -alk-NR$_{52}$R$_{53}$, alkylsulfanyl, alkylsulfinyl, alkylsulfonyl, alkylsulfanylalkyl, alkylsulfinylalkyl, alkylsulfonylalkyl or hydroxyalkyl;

$R_{47}$ is —C(R$_{54}$)(R$_{55}$)-Het$_3$, Het$_3$, —C(R$_{54}$)(R$_{55}$)—Ar$_3$, Ar$_3$, cycloalkyl or norbornyl;

$R_{48}$ is hydrogen or hydroxyalkyl, -alk-COOalk, -alk-CONR$_{50}$R$_{51}$, -alk-NR$_{50}$R$_{51}$, alkoxy; Ar$_3$, Het$_3$, —CH$_2$Ar$_3$, —CH$_2$Het$_3$ or alkyl, optionally substituted with one or more halogen;

$R_{49}$ is hydroxyalkyl, -alk-COOalk, -alk-CONR$_{50}$R$_{51}$, -alk-NR$_{50}$R$_{51}$, alkoxy, Ar$_3$, Het$_3$, —CH$_2$Ar$_3$, —CH$_2$Het$_3$ or alkyl optionally substituted with one or more halogen;

$R_{50}$ and $R_{51}$, which are identical or different, independently are hydrogen or alkyl; or $R_{50}$ and $R_{51}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl;

$R_{52}$ and $R_{53}$, which are identical or different, independently are hydrogen or alkyl, —COOalk, cycloalkyl, alkylcycloalkyl, -alk-O-alk or hydroxyalkyl; or $R_{52}$ and $R_{53}$ taken together with the nitrogen atom to which they are attached form a saturated or unsaturated and mono- or bicyclic heterocycle having 3 to 10 ring members optionally comprising another heteroatom chosen from oxygen, sulfur and nitrogen and optionally being substituted by one or more alkyl, —COalk, —COOalk, —CO—NHalk, —CS—NHalk, oxo, hydroxyalkyl, -alk-O-alk or —CO—NH$_2$;

$R_{54}$ is hydrogen, hydroxyalkyl, -alk-COOalk, -alk-CONR$_{50}$R$_{51}$, -alk-NR$_{50}$R$_{51}$, alkoxyalkyl, Ar$_3$, Het$_3$, —CH$_2$Ar$_3$, —CH$_2$Het$_3$ or alkyl optionally substituted with one or more halogen;

$R_{55}$ is hydrogen or hydroxyalkyl, -alk-COOalk, -alk-CONR$_{50}$R$_{51}$, -alk-NR$_{50}$R$_{51}$, alkoxyalkyl or alkyl optionally substituted with one or more halogen; or $R_{54}$ and $R_{55}$ taken together with the carbon atom to which they are attached form a saturated mono- or bicyclic ring having 3 to 10 ring members optionally comprising another heteroatom chosen from oxygen, sulfur and nitrogen and optionally being substituted by one or more alkyl;

$Ar_3$ is phenyl, naphthyl or indenyl, optionally being substituted by one or more halogen, alkyl, alkoxy, —CO-alk, cyano, —COOH, —COOalk, —CONR$_{56}$R$_{57}$, —CO—NH—NR$_{58}$R$_{59}$, alkylsulfanyl, alkylsulfinyl, alkylsulfonyl, -alk-NR$_{58}$R$_{59}$, —NR$_{58}$R$_{59}$, alkylthioalkyl, formyl, CF$_3$, OCF$_3$, Het$_3$, —O-alk-NH-cycloalkyl, SO$_2$NH$_2$, hydroxyl, hydroxyalkyl, —NH-COalk or —NHCOOalk or on 2 adjacent carbon atoms by dioxymethylene;

Het₃ is a saturated or unsaturated and mono- or bicyclic heterocycle having 3 to 10 ring members and comprising one or more heteroatoms chosen from oxygen, sulfur and nitrogen optionally substituted by one or more alkyl, alkoxy, halogen, alkoxycarbonyl, oxo or hydroxyl, the nitrogenous heterocycles optionally being in their N-oxidized form;

$R_{56}$ and $R_{57}$, which are identical or different, independently are hydrogen or alkyl radical; or $R_{56}$ and $R_{57}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl;

$R_{58}$ and $R_{59}$, which are identical or different, independently are hydrogen or alkyl; or $R_{58}$ and $R_{59}$ taken together with the nitrogen atom to which they are attached form a saturated mono- or bicyclic heterocycle having 3 to 10 ring members optionally comprising another heteroatom chosen from oxygen, sulfur and nitrogen and optionally being substituted by one or more alkyl;

alk is an alkyl or alkylene radical; and wherein the alkyl, alkylene and alkoxy radicals have straight or branched chains and comprise 1 to 6 carbon atoms, the cycloalkyl radicals comprise 3 to 10 carbon atoms and the heterocycloalkyl and heterocyclenyl radicals comprise 3 to 10 carbon atoms; or an optical isomer thereof or a pharmaceutically acceptable salt thereof.

2. The composition according to claim 1, wherein the compound of formula (I) is chosen from the following compounds:

N-{1-[bis(4-chlorophenyl)methyl]azetidin-3-yl}-N-(pyrid-3-yl)methylsulfonamide or N-{1-[bis(4-chlorophenyl)methyl]azetidin-3-yl}-N-(3,5-difluorophenyl)methylsulfonamide, or a pharmaceutically acceptable salt thereof.

3. The composition according to claim 1, wherein the dopaminergic agonist is levodopa and the CB1 antagonist is N-{1-[bis(4-chlorophenyl)methyl]azetidin-3-yl}-N-(3,5-difluorophenyl)-methylsulfonamide.

4. A pharmaceutical composition comprising a dopaminergic agonist and one or more CB1 antagonists of formula (I) as defined in claim 1 in combination with a compatible and pharmaceutically acceptable vehicle.

5. The pharmaceutical composition according to claim 4, wherein the compound of formula (I) as defined in claim 1 is chosen from the following compounds:

N-{1-[bis(4-chlorophenyl)methyl]azetidin-3-yl}-N-(pyrid-3-yl)methylsulfonamide, or N-{1-[bis(4-chlorophenyl)methyl]azetidin-3-yl}-N-(3,5-difluorophenyl)methylsulfonamide, or a pharmaceutically acceptable salt thereof.

6. The pharmaceutical composition according to claim 4, wherein the dopaminergic agonist is levodopa and the CB1 antagonist is N-{1-[bis(4-chlorophenyl)methyl]azetidin-3-yl}-N-(3,5-difluorophenyl)methylsulfonamide.

7. The pharmaceutical composition according to claim 4 wherein the CB1 antagonist of formula (I) as defined in claim 1 is present in an amount of from about 0.1 mg to about 500 mg.

* * * * *